US007939249B2

(12) United States Patent
Parthasarathy et al.

(10) Patent No.: US 7,939,249 B2
(45) Date of Patent: May 10, 2011

(54) METHODS FOR NUCLEIC ACID ISOLATION AND KITS USING A MICROFLUIDIC DEVICE AND CONCENTRATION STEP

(75) Inventors: Ranjani V. Parthasarathy, Woodbury, MN (US); Katya Ericson, Fairburn, GA (US); William Bedingham, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1279 days.

(21) Appl. No.: 10/852,085

(22) Filed: May 24, 2004

(65) Prior Publication Data

US 2005/0142663 A1 Jun. 30, 2005

Related U.S. Application Data

(60) Provisional application No. 60/532,523, filed on Dec. 24, 2003.

(51) Int. Cl.
*C12Q 1/68* (2006.01)
(52) U.S. Cl. .......................................................... 435/6
(58) Field of Classification Search .................. None
See application file for complete search history.

(56) References Cited

U.S. PATENT DOCUMENTS

| 3,157,635 | A | 11/1964 | Tanaka et al. |
|---|---|---|---|
| 4,153,661 | A | 5/1979 | Ree et al. |
| 4,373,519 | A | 2/1983 | Errede et al. |
| 4,399,009 | A | 8/1983 | Chisholm |
| 4,399,235 | A | 8/1983 | Raley, Jr. et al. |
| 4,460,642 | A | 7/1984 | Errede et al. |
| 4,483,920 | A | 11/1984 | Gillespie et al. |
| 4,539,256 | A | 9/1985 | Shipman |
| 4,565,663 | A | 1/1986 | Errede et al. |
| 4,619,897 | A | 10/1986 | Hato et al. |
| 4,726,989 | A | 2/1988 | Mrozinski |
| 4,737,560 | A | 4/1988 | Heilmann et al. |
| 4,757,014 | A | 7/1988 | Hendrickson et al. |
| 4,780,367 | A | 10/1988 | Lau et al. |
| 4,810,381 | A | 3/1989 | Hagen et al. |
| 4,839,296 | A | 6/1989 | Kennedy et al. |
| 4,855,234 | A | 8/1989 | Hendrickson et al. |
| 4,906,378 | A | 3/1990 | Hagen et al. |
| 4,923,978 | A | 5/1990 | McCormick |
| 4,954,444 | A | 9/1990 | Eveleigh et al. |
| 4,957,943 | A | 9/1990 | McAllister et al. |
| 4,971,736 | A | 11/1990 | Hagen et al. |
| 5,010,183 | A | 4/1991 | Macfarlane |
| 5,011,861 | A | 4/1991 | Coull et al. |
| 5,015,373 | A | 5/1991 | Carr et al. |
| 5,019,232 | A | 5/1991 | Wilson et al. |
| 5,030,697 | A | 7/1991 | Hugl et al. |
| 5,071,610 | A | 12/1991 | Hagen et al. |
| 5,079,155 | A | 1/1992 | Cox et al. |
| 5,108,597 | A | 4/1992 | Funkenbusch et al. |
| 5,141,634 | A | 8/1992 | Carr et al. |
| 5,147,539 | A | 9/1992 | Hagen et al. |
| 5,182,016 | A | 1/1993 | Funkenbusch et al. |
| 5,182,083 | A | 1/1993 | Barker et al. .................. 422/63 |
| 5,182,377 | A | 1/1993 | Manos et al. |
| 5,183,705 | A | 2/1993 | Birkholz et al. |
| 5,187,066 | A | 2/1993 | Becker et al. |
| 5,187,083 | A | 2/1993 | Mullis |
| 5,200,471 | A | 4/1993 | Coleman et al. |
| 5,205,929 | A | 4/1993 | Carr et al. |
| 5,207,915 | A | 5/1993 | Hagen et al. |
| 5,234,809 | A | 8/1993 | Boom et al. |
| 5,238,621 | A | 8/1993 | Hagen et al. |
| 5,264,184 | A | 11/1993 | Aysta et al. |
| 5,271,833 | A | 12/1993 | Funkenbusch et al. |
| 5,279,742 | A | 1/1994 | Markell et al. |
| 5,284,940 | A | 2/1994 | Lin et al. ......................... 536/25 |
| 5,294,668 | A | 3/1994 | Babu |
| 5,328,758 | A | 7/1994 | Markell et al. |
| 5,334,316 | A | 8/1994 | Bruening et al. |
| 5,344,701 | A | 9/1994 | Gagnon et al. |
| 5,346,619 | A | 9/1994 | Funkenbusch et al. |
| 5,349,125 | A | 9/1994 | Holton et al. |
| 5,376,528 | A | 12/1994 | King et al. |
| 5,380,901 | A | 1/1995 | Antonucci et al. |
| RE34,910 | E | 4/1995 | Funkenbusch et al. |
| 5,405,951 | A | 4/1995 | Woodard |
| 5,415,779 | A | 5/1995 | Markell et al. |
| 5,438,127 | A | 8/1995 | Woodard et al. |
| 5,438,128 | A | 8/1995 | Nieuwkerk et al. |

(Continued)

FOREIGN PATENT DOCUMENTS

DE 197 31 670 A1 1/1999

(Continued)

OTHER PUBLICATIONS

Daugherty "Using ion Exchange Chromatography to Separate Proteins." Access Excellence Activities Exchange at the National Health Museum, Washington, D.C. 2007. Available online [retrieved Apr. 17, 2007]. Retrieved from the Internet: <http://www.accessexcellence.org/AE/AEC/AEF/1994/daugherty_ion.html>; 4 pgs.
Daughton "Quantitaion of Acrylimide (and Polyacrylimide): Critical Review of Methods for Trace Determination/Formulation Analysis & Future-research Recommendations." Final Report No. CGD-02/88. Prepared for The California Public Health Foundation: Berkeley, CA. Jun. 23, 1988. Title page and table of contents only; 5 pgs.
Kube et al. "Quantitative DNA by Slot Blot Analysis: Inhibition of DNA Binding to Membranes by Magnesium ions." 1997 *Nucleic Acids Research* 25(16):3375-3376.
Emmer Asa et al.; "Wall deactivation with fluorosurfactants for capillary electrophoretic analysis of biomolecules" *Electroophoresis*, vol. 22, No. 4, Feb. 2001; pp. 660-665, XP002325650; ISSN: 0173-0835, p. 664.
Cornett, J. et al.; "Cellular Lysis of *Streptococcus faecalis* Induced with Triton X-100"; Journal of Bacteriology, vol. 135, No. 1, Jul. 1978, p. 153-160.
Kapustin, D.V. et al.; "Composite fluorine polymer-containing sorbents for isolation and purification of biopolymers" Bioorg Khim. Nov. 1998; 24 (11) pp. 868-876 (Abstract Only).
U.S. Appl. No. 10/417,609, filed Apr. 17, 2003, Parthasarathy et al.
U.S. Appl. No. 10/734,717, filed Dec. 12, 2003, Bedingham et al.

(Continued)

*Primary Examiner* — Christopher M. Babic
(74) *Attorney, Agent, or Firm* — Nicole J. Einerson

(57) ABSTRACT

The present invention provides methods and kits for isolating nucleic acid from a sample, preferably from a biological sample, using a microfluidic device and a concentration step.

34 Claims, 1 Drawing Sheet

U.S. PATENT DOCUMENTS

| | | | |
|---|---|---|---|
| 5,438,129 A | 8/1995 | Woodard et al. | |
| 5,451,453 A | 9/1995 | Gagnon et al. | |
| 5,464,541 A | 11/1995 | Aysta et al. | |
| 5,472,600 A | 12/1995 | Ellefson et al. | |
| 5,486,358 A | 1/1996 | Coleman et al. | |
| 5,510,084 A | 4/1996 | Cros et al. | |
| 5,512,439 A | 4/1996 | Hornes et al. | |
| 5,525,319 A | 6/1996 | Woodard et al. | |
| 5,543,305 A | 8/1996 | Cummins et al. | |
| 5,585,236 A | 12/1996 | Bonn et al. | |
| 5,595,649 A | 1/1997 | Markell et al. | |
| 5,610,287 A | 3/1997 | Nikiforov et al. | |
| 5,620,663 A | 4/1997 | Aysta et al. | |
| 5,620,852 A | 4/1997 | Lin et al. | |
| 5,625,053 A | 4/1997 | Kresheck et al. | |
| 5,633,290 A | 5/1997 | Frechet et al. | |
| 5,635,060 A | 6/1997 | Hagen et al. | |
| 5,637,687 A | 6/1997 | Wiggins | |
| 5,639,372 A | 6/1997 | Hagen et al. | |
| 5,639,599 A * | 6/1997 | Ryder et al. | 435/5 |
| 5,688,370 A | 11/1997 | Hagen et al. | |
| 5,691,208 A | 11/1997 | Miltenyi et al. | |
| 5,702,610 A | 12/1997 | Hagen et al. | |
| 5,709,943 A | 1/1998 | Coleman et al. | |
| 5,738,790 A | 4/1998 | Hagen et al. | |
| 5,741,828 A | 4/1998 | Stoy et al. | |
| 5,786,208 A | 7/1998 | Clark et al. | |
| 5,786,219 A * | 7/1998 | Zhang et al. | 436/523 |
| 5,801,237 A | 9/1998 | Johansson | |
| 5,804,684 A | 9/1998 | Su | |
| 5,834,583 A | 11/1998 | Hancock et al. | |
| 5,856,379 A | 1/1999 | Shiratsuchi et al. | |
| 5,869,002 A | 2/1999 | Limon et al. | 422/58 |
| 5,882,521 A | 3/1999 | Bouvier et al. | |
| 5,904,848 A | 5/1999 | Wong et al. | |
| 5,919,626 A | 7/1999 | Shi et al. | |
| 5,976,367 A | 11/1999 | Bouvier et al. | |
| 5,976,468 A | 11/1999 | Godec et al. | 422/100 |
| 5,993,935 A | 11/1999 | Rasmussen et al. | |
| 5,997,818 A | 12/1999 | Hacker et al. | |
| 5,999,935 A | 12/1999 | Clark et al. | |
| 6,007,690 A | 12/1999 | Nelson et al. | |
| 6,048,457 A | 4/2000 | Kopaciewicz et al. | |
| 6,048,550 A | 4/2000 | Chan et al. | |
| 6,063,589 A * | 5/2000 | Kellogg et al. | 435/24 |
| 6,063,838 A | 5/2000 | Patnode et al. | |
| 6,068,751 A | 5/2000 | Neukermans et al. | |
| 6,071,406 A | 6/2000 | Tsou | |
| 6,074,827 A | 6/2000 | Nelson et al. | |
| 6,074,927 A | 6/2000 | Kepler et al. | |
| 6,084,091 A | 7/2000 | Müller et al. | |
| 6,093,558 A | 7/2000 | Seed et al. | |
| 6,093,559 A | 7/2000 | Bookbinder et al. | |
| RE36,811 E | 8/2000 | Markell et al. | |
| 6,103,199 A | 8/2000 | Bjornson et al. | |
| 6,143,247 A | 11/2000 | Sheppard, Jr. et al. | 422/63 |
| 6,143,248 A | 11/2000 | Kellogg et al. | 422/72 |
| 6,168,948 B1 * | 1/2001 | Anderson et al. | 435/287.2 |
| 6,197,595 B1 | 3/2001 | Anderson et al. | |
| 6,200,474 B1 | 3/2001 | Kopaciewicz et al. | |
| 6,207,251 B1 | 3/2001 | Balsimo et al. | |
| 6,254,780 B1 | 7/2001 | Bouvier et al. | |
| 6,261,497 B1 | 7/2001 | Wong et al. | |
| 6,265,168 B1 | 7/2001 | Gjerde et al. | |
| 6,265,224 B1 | 7/2001 | Collis et al. | |
| 6,277,488 B1 | 8/2001 | Kobe et al. | |
| 6,284,113 B1 | 9/2001 | Bjornson et al. | |
| 6,302,134 B1 | 10/2001 | Kellogg et al. | 137/74 |
| 6,306,273 B1 | 10/2001 | Wainright et al. | |
| 6,319,469 B1 | 11/2001 | Mian et al. | |
| 6,344,326 B1 | 2/2002 | Nelson et al. | |
| 6,348,336 B1 * | 2/2002 | Matveld et al. | 435/91.2 |
| 6,383,783 B1 | 5/2002 | Haddad | |
| 6,428,707 B1 | 8/2002 | Berg et al. | |
| 6,440,725 B1 | 8/2002 | Pourahmadi et al. | 435/288 |
| 6,450,047 B2 | 9/2002 | Swedberg et al. | |
| 6,451,260 B1 | 9/2002 | Düsterhoft et al. | |
| 6,465,225 B1 | 10/2002 | Fuhr et al. | 435/173 |
| 6,479,300 B1 | 11/2002 | Jiang et al. | |
| 6,504,021 B2 | 1/2003 | Kristyanne et al. | |
| 6,527,432 B2 | 3/2003 | Kellogg et al. | 366/182 |
| 6,532,997 B1 | 3/2003 | Bedingham et al. | |
| 6,537,502 B1 | 3/2003 | Shukla et al. | |
| 6,544,734 B1 * | 4/2003 | Briscoe et al. | 435/6 |
| 6,548,788 B2 | 4/2003 | Kellogg et al. | 219/543 |
| 6,582,662 B1 | 6/2003 | Kellogg et al. | 422/72 |
| 6,617,136 B2 | 9/2003 | Parthasarathy et al. | |
| 6,627,159 B1 | 9/2003 | Bedingham et al. | 422/100 |
| 6,632,399 B1 | 10/2003 | Kellogg et al. | |
| 6,664,104 B2 | 12/2003 | Pourahmadi et al. | |
| 6,664,354 B2 | 12/2003 | Savu et al. | |
| 6,692,596 B2 | 2/2004 | Moll et al. | |
| 6,720,187 B2 | 4/2004 | Bedingham et al. | |
| 6,723,236 B2 | 4/2004 | Fisk et al. | |
| 6,730,516 B2 | 5/2004 | Jedrzejewski et al. | |
| 6,734,401 B2 | 5/2004 | Bedingham et al. | |
| 6,780,818 B2 | 8/2004 | Gundel et al. | |
| 6,790,642 B2 | 9/2004 | Haddad | |
| 6,814,935 B2 | 11/2004 | Harms et al. | |
| 6,833,238 B2 | 12/2004 | Ramstad et al. | |
| 6,852,781 B2 | 2/2005 | Savu et al. | |
| 6,875,348 B2 | 4/2005 | Zare et al. | |
| 6,919,058 B2 | 7/2005 | Andersson et al. | |
| 6,998,271 B2 | 2/2006 | Wong et al. | |
| 7,026,168 B2 | 4/2006 | Bedingham et al. | |
| 7,138,436 B2 | 11/2006 | Tan et al. | |
| 7,189,368 B2 | 3/2007 | Andersson et al. | |
| 7,192,560 B2 | 3/2007 | Parthasarathy et al. | |
| 7,214,348 B2 | 5/2007 | Desmond et al. | |
| 7,311,880 B2 | 12/2007 | Perman et al. | |
| 7,322,254 B2 | 1/2008 | Bedingham et al. | |
| 7,374,724 B2 | 5/2008 | Ingenhoven et al. | |
| 2001/0045000 A1 | 11/2001 | Gundel et al. | |
| 2002/0046966 A1 | 4/2002 | Muscate-Magnussen | |
| 2002/0047003 A1 | 4/2002 | Bedingham et al. | 219/388 |
| 2002/0048533 A1 | 4/2002 | Harms et al. | |
| 2002/0064885 A1 | 5/2002 | Bedingham et al. | |
| 2002/0155034 A1 | 10/2002 | Perman et al. | |
| 2002/0182114 A1 | 12/2002 | Ingenhoven et al. | |
| 2003/0011092 A1 | 1/2003 | Tan et al. | |
| 2003/0013203 A1 | 1/2003 | Jedrzejewski et al. | |
| 2003/0017567 A1 | 1/2003 | Parthasarathy et al. | |
| 2003/0018177 A1 | 1/2003 | Haddad | |
| 2003/0044322 A1 | 3/2003 | Andersson et al. | 422/100 |
| 2003/0053934 A1 | 3/2003 | Andersson et al. | |
| 2003/0062310 A1 | 4/2003 | Zare et al. | |
| 2003/0120062 A1 | 6/2003 | Parthasarathy et al. | |
| 2003/0138779 A1 | 7/2003 | Parthasarathy et al. | |
| 2003/0139549 A1 | 7/2003 | Savu et al. | |
| 2003/0139550 A1 | 7/2003 | Savu et al. | |
| 2003/0152915 A1 | 8/2003 | Kellogg et al. | 422/99 |
| 2003/0155034 A1 | 8/2003 | De Beukeleer et al. | |
| 2003/0228701 A1 | 12/2003 | Wong et al. | |
| 2003/0228706 A1 | 12/2003 | Ramstad et al. | |
| 2004/0016702 A1 | 1/2004 | Hennessy et al. | |
| 2004/0018116 A1 | 1/2004 | Desmond et al. | |
| 2004/0018559 A1 | 1/2004 | Lau et al. | |
| 2004/0171170 A1 | 9/2004 | Sandell | |
| 2004/0209258 A1 | 10/2004 | Parthasarathy et al. | |
| 2005/0126312 A1 | 6/2005 | Bedingham et al. | |
| 2005/0130177 A1 | 6/2005 | Bedingham et al. | |
| 2005/0142563 A1 | 6/2005 | Haddad et al. | |
| 2005/0142570 A1 | 6/2005 | Parthasarathy et al. | |
| 2005/0142571 A1 | 6/2005 | Parthasarathy et al. | |
| 2006/0013732 A1 | 1/2006 | Parthasarathy et al. | |
| 2007/0148687 A1 | 6/2007 | Bedingham et al. | |
| 2007/0160504 A1 | 7/2007 | Parthasarathy et al. | |
| 2010/0167304 A1 | 7/2010 | Bedingham et al. | |

FOREIGN PATENT DOCUMENTS

| | | |
|---|---|---|
| DE | 197 31 670 C2 | 6/2000 |
| EP | 0 281 368 A | 9/1988 |
| EP | 0 309 259 A2 | 3/1989 |
| EP | 0 309 259 A3 | 3/1989 |
| EP | 0 389 063 A2 | 9/1990 |
| EP | 0 389 063 A3 | 9/1990 |
| EP | 0 409 432 A2 | 1/1991 |

| | | | |
|---|---|---|---|
| EP | 0 409 432 A3 | 1/1991 |
| EP | 0 426 488 A1 | 5/1991 |
| EP | 0 447 362 A1 | 9/1991 |
| EP | 0 524 864 A1 | 1/1993 |
| EP | 0 572 907 A2 | 12/1993 |
| EP | 0 572 907 A3 | 12/1993 |
| EP | 0 309 259 B1 | 6/1994 |
| EP | 0 426 488 B1 | 4/1997 |
| EP | 0770689 A2 | 5/1997 |
| EP | 0 389 063 B1 | 8/1997 |
| EP | 0 524 864 B1 | 5/1998 |
| EP | 0 897 978 A2 | 2/1999 |
| EP | 0 897 978 A3 | 2/1999 |
| EP | 1 459 795 | 9/2004 |
| JP | 2-268-682 | 11/1990 |
| JP | 2-295-485 | 12/1990 |
| JP | 7-265718 | 10/1995 |
| JP | 9-302-034 | 11/1997 |
| JP | 2006-505766 | 2/2006 |
| WO | 90/10637 A1 | 9/1990 |
| WO | 92/18514 A1 | 10/1992 |
| WO | WO 92/16659 A1 | 10/1992 |
| WO | 94/00464 A1 | 1/1994 |
| WO | WO 95/19781 A | 7/1995 |
| WO | 95/24505 A1 | 9/1995 |
| WO | 97/07239 A1 | 2/1997 |
| WO | WO 97/21090 A | 6/1997 |
| WO | 97/27325 A2 | 7/1997 |
| WO | 97/27325 A3 | 7/1997 |
| WO | 98/04909 A1 | 2/1998 |
| WO | WO 98/12351 A1 | 3/1998 |
| WO | WO 98/39094 A1 | 9/1998 |
| WO | 99/15876 A1 | 4/1999 |
| WO | 99/15888 A1 | 4/1999 |
| WO | 99/22021 A1 | 5/1999 |
| WO | 99/23487 A1 | 5/1999 |
| WO | 99/28504 A1 | 6/1999 |
| WO | 99/39120 A1 | 8/1999 |
| WO | 99/40174 A1 | 8/1999 |
| WO | 99/46591 A2 | 9/1999 |
| WO | 99/46591 A3 | 9/1999 |
| WO | WO 99/58664 A1 | 11/1999 |
| WO | 00/45180 A1 | 8/2000 |
| WO | 00/62051 A2 | 10/2000 |
| WO | 00/62051 A3 | 10/2000 |
| WO | 00/68336 A1 | 11/2000 |
| WO | 01/03149 A1 | 1/2001 |
| WO | 01/12327 A | 2/2001 |
| WO | 01/21632 A1 | 3/2001 |
| WO | 01/25490 A1 | 4/2001 |
| WO | WO 01/25491 A1 | 4/2001 |
| WO | 01/30873 A1 | 5/2001 |
| WO | 01/37291 A1 | 5/2001 |
| WO | 01/38516 A1 | 5/2001 |
| WO | 01/38865 A1 | 5/2001 |
| WO | WO 01/30995 A | 5/2001 |
| WO | WO 01/62976 A1 | 8/2001 |
| WO | 01/68240 A2 | 9/2001 |
| WO | 01/68240 A3 | 9/2001 |
| WO | 01/68913 A2 | 9/2001 |
| WO | 01/68913 A3 | 9/2001 |
| WO | 01/71732 A2 | 9/2001 |
| WO | 01/71732 A3 | 9/2001 |
| WO | 02/00347 | 1/2002 |
| WO | 02/44400 A2 | 6/2002 |
| WO | 02/44400 A3 | 6/2002 |
| WO | WO 03/054509 A2 | 7/2003 |
| WO | WO 03/054509 A3 | 7/2003 |
| WO | WO 03/054510 A2 | 7/2003 |
| WO | WO 03/054510 A3 | 7/2003 |
| WO | WO 03/058224 A1 | 7/2003 |
| WO | WO 03/059484 | 7/2003 |
| WO | WO 03/087827 | 10/2003 |
| WO | 2004/009851 A2 | 1/2004 |
| WO | 2004/010760 A2 | 2/2004 |
| WO | 2004/011141 A1 | 2/2004 |
| WO | 2004/011142 A1 | 2/2004 |
| WO | 2004/011592 A2 | 2/2004 |
| WO | 2004/011592 A3 | 2/2004 |
| WO | 2004/011681 A1 | 2/2004 |
| WO | WO 2004/094672 A1 | 11/2004 |
| WO | WO 2005/005045 A | 1/2005 |

OTHER PUBLICATIONS

U.S. Appl. No. 11/684,656, filed Mar. 12, 2007, Bedingham et al.
U.S. Appl. No. 11/709,373, filed Feb. 22, 2007, Parthasarathy et al.
Yamaguchi Y et al. "*Increased Sensitivity for Detection of Human Cytomegalovirus in Urine by Removal of Inhibitors for the Polymerase Chain Reaction*", Journal of Virological Methods, vol. 37, No. 2, 1992, pp. 209-218.
Behzadbehbahani A. et al. "*Detection of BK Virus in Urine by Polymerase Chain Reaction: A Comparison of DNA Extraction Methods*", Journal of Virological Methods, vol. 67, 1997, pp. 161-166.
3M Material Safety Data Sheet for FC-4430 FLUORAD™ Fluorosurfactant (9 pgs) (May 7, 2003).
3M Material Safety Data Sheet for 3M™ FLUORAD™ Fluorosurfactant FC-4432 (9 pgs) (May 21, 2003).
"ABI Prism® BigDye™ Terminators v3.0 Cycle Sequencing Kit," product information [online]. Applied Biosystems, 2000, 2001 [retrieved Dec. 3, 2001]. Retrieved from the Internet: <URL:http://www.appliedbiosystems.com/products/productdetail.cfm?id=81>, p. 1.
Al-Soud et al.; "Purification and Characterization of PCR-Inhibitory Components in Blood Cells," *Journal of Clinical Microbiology*; vol. 39(2); pp. 485-493 (2001).
Altschuler et al.; "Benchmarks: Plasmid DNA Isolation Utilizing a Novel Nonionic Detergent," *BioTechniques*; vol. 17(3); pp. 434, 436 (1994).
American Society of Testing Materials, "ASTM D 570-98, Standard Test Method for Water Absorption of Plastics," *Annual Book of ASTM Standards*, pp. 31-33 and Title page (Jan. 2001).
AutoSeq96 Dye Terminator Clean-up Kit / Adapter Plate for AutoSeq96, product catalogue [online]. Amersham Biosciences, 2001 [retrieved Dec. 3, 2001]. Retrieved from the Internet: <URL:http://www.apbiotech.com/stiboasp/showmodule.asp?nModuleid=164360>, pp. 1-2.
Bartl et al.; "Simple and Broadly Applicable Preparation by Use of Magnetic Glass Particles," *Clin Chem Lab Med*, vol. 36(8), pp. 557-559 (1998).
"BLAST," National Institutes of Health [online] United States, [retrieved Oct. 23, 2000]. Retrieved from the Internet:<URL:http://www.ncbi.nlm.nih.gov/BLAST>, 2 pgs.
Bischoff et al.; "Isolation of Specific tRNAs Using an Ionic-Hydrophobic Mixed-Mode Chromatographic Matrix," *Analytical Biochemistry*; vol. 151; pp. 526-533 (1985).
QIAamp® DSP DNA Blood Mini Kit Handbook, 28 pages (Jan. 2004).
Boom et al., "Rapid and Simple Method for Purification of Nucleic Acids," *Journal of Clinical Microbiology*, Mar. 1990; vol. 28, No. 3; pp. 495-503, Publication page, and Title page.
Breadmore et al.; "Microchip-Based Purification of DNA from Biological Samples," *Analytical Chemistry*; vol. 75(8); pp. 1880-1886 (2003).
Brezinski; "Laying the foundation for New Technologies 3M Creates a new building block for its fluorosurfactants," *Paintings and Coatings Industry*, (Jan. 2003).
Buffone et al.; "Isolation of DNA from Biological Specimens without Extraction with Phenol," *Clininical Chemistry*, vol. 31(1), pp. 164-165 (1985).
Burckhardt; "Amplification of DNA From Whole Blood," PCR Methods and Applications, *Cold Spring Harbor Laboratory Press*, vol. 3, No. 4., pp. 239-243 (Feb. 1994).
Rudbeck et al.; "Benchmarks: Rapid, Simple Alkaline Extraction of Human Genomic DNA from Whole Blood, Buccal Epithelial Cells, Semen and Forensic Stains for PCR," *BioTechniques*, vol. 25(4), pp. 588-589, 592 (1998).
Fraker et al., *Biochem. Biophys. Res. Commun.*, vol. 80, pp. 849-857 (1978).

Huber et al.; "High-performance liquid chromatographic separation of detrilyated oligonucleotides on highly cross-linked poly-(styrene-divinylbenzene) particles," *Journal of Chromatography*; vol. 599; pp. 113-118 (1992).

Jeffreys, et al., "DNA 'Fingerprints' and Segregation Analysis of Multiple Markers in Human Pedigrees," *American Journal of Human Genetics*, vol. 39, pp. 11-24 (1986).

Kogan et al.; "An Improved Method for Prenatal Diagnosis of Genetic Diseases by Analysis of Amplified DNA Sequences, Application to Hemophilia A," *New England Journal of Medicine*, vol. 317, pp. 985-990 (1987).

Kroschwitz et al., (Eds.); *Kirk-Othmer Encyclopedia of Chemical Technology, 4th Ed.*; John Wiley and Sons; NY; vol. 23; pp. 506-523 (1997).

Nielsen et al.; "Peptide nucleic acid (PNA), a DNA mimic with a pseudopetide backbone," *Chemical Society Review*; vol. 26; pp. 73-78 (1997).

Tian et al.; "Evaluation of Silica Resins for Direct and Efficient Extraction of DNA from Complex Biological Matrices in a Miniaturized Format," *Analytical Biochemistry*, vol. 283, pp. 175-191 (2000).

"Porex Corporate Profile," [online]. Porex Corporation, 2001 [retrieved Dec. 5, 2001]. Retrieved from the Internet: <URL:http://www.porex.com/english/corporate/index.asp>, pp. 1-3.

"Porex Products Group," product profile [online]. Porex Corporation, 2001 [retrieved Dec. 5, 2001]. Retrieved from the Internet: <URL:http://www.porex.com/english/porous/index.asp>, pp. 1-2.

Product Information Brochure, "DuPont™ Zonyl® Fluoroadditives for Coatings Technical Information," (4 pgs) (Mar. 2003).

Product Information Brochure "3M Novec™ Fluorosurfactants FC-4430 / 3M™ Fluorad™ Fluorosurfactants are now 3M™ Novec™ Fluorosurfactants," (4 pgs), (Oct. 2003).

Product Information Brochure "Zonyl® Flurosurfactants," (2 pgs), obtained from the Internet on Dec. 1, 2003, <URL:http://web.singnet.com.sg/~paseden/dupont6.htm> (Apr. 2003).

"Purification so fast it'll make your head spin: RapTract Dye Terminator Removal Kit," Prolinx Product Information, Bothell, WA, 2000. pp. 1-6.

"3M Empore Products 96-Well Plates," product listing [online]. 3M Corporation, 1999 [retrieved Dec. 5, 2001]. Retrieved from the Internet: <URL:http://www.mmm.com/empore/formats/Plates/sorbavlb/index.htm>, pp. 1-2.

"3M Empore Products Empore 96-Well Plates" SPE Extraction Disk Plates & Filter Plates, 3M Extraction Disk Plates for SPE, product listing [online]. 3M Corporation, 1999 [retrieved Dec. 5, 2001]. Retrieved from the Internet: <URL:http://www.mmm.com/empore/formats/Plates/index.htm>, pp. 1-2.

Takeuchi et al., "Ion Chromatography Using Anion Exchangers Modified with Anionic Polysaccharides," LCGC Magazine [online]. LCGC North America, 2001 [retrieved Oct. 2, 2001]. Retrieved from the Internet: <URL:http://www.lcgcmag.com/articles/0004_articles/0004_Takeuchi/0004_Takeuchi.asp>, pp. 1-12.

Tong, et al., "Solid-Phase Method for the Purification of DNA Sequencing Reactions," *Anal Chem*, 1992; vol. 64, No. 22; pp. 2672-2677, Publication page, and Title page.

Co-related U.S. Appl. No. 10/417,609, filed Apr. 17, 2003 entitled "Methods and Devices for Removal of Organic Molecules from Biological Mixtures Using an Anion Exchange Material that Includes a Polyoxyalkylene".

Co-related U.S. Appl. No. 60/532,404, filed Dec. 24, 2003 entitled "Methods and Kits for Reducing Nonspecific Binding of Molecules to a Surface".

Co-related U.S. Appl. No. 10/852,642, filed May 24, 2004 entitled "Variable Valve Apparatus and Methods".

Co-related U.S. Appl. No. 60/532,523, filed Dec. 24, 2003 entitled "Methods for Nucleic Acid Isolation and Kits".

Co-related U.S. Appl. No. 10/852,645, filed May 24, 2004 entitled "Methods for Nucleic Acid Isolation and Kits Using Solid Phase Material".

Co-related U.S. Appl. No. 60/532,523, filed Dec. 24, 2003 entitled "Methods and Kits for Reducing Nonspecific Binding of Molecules to a Surface".

Co-related U.S. Appl. No. 10/810,738, filed Mar. 26, 2004 entitled "Materials, Methods, and Kits for Reducing Nonspecific Binding of Molecules to a Surface".

Co-related U.S. Appl. No. 10/852,022, filed May 24, 2004 entitled "Methods for Nucleic Acid Isolation and Kits Using a Microfluidic Device and Sedimenting Agent".

Garcia, A. et al.; "Comparison of Two Leukocyte Extraction Methods for Cytomegalovirus Antigenemia Assay"; Journal of Clinical Microbiology, Jan. 1996, p. 182-184.

Wang, Hailin et al., *Short Protocols in Molecular Biology*, Science Press, (1998).

U.S. Office Action in U.S. Appl. No. 12/719,704, dated Mar. 4, 2011; 30 pgs.

\* cited by examiner

METHODS FOR NUCLEIC ACID ISOLATION AND KITS USING A MICROFLUIDIC DEVICE AND CONCENTRATION STEP

CROSS-REFERENCE TO RELATED CASES

The present application claims priority to U.S. Provisional Application Ser. No. 60/532,523, filed on Dec. 24, 2003, which is incorporated herein by reference in its entirety.

BACKGROUND

The isolation and purification of nucleic acids (DNA and RNA, for example) from complex matrices such as blood, tissue samples, bacterial cell culture media, and forensic samples is an important process in genetic research, nucleic acid probe diagnostics, forensic DNA testing, and other areas that require amplification of the nucleic acids. A variety of methods of preparing nucleic acids for amplification procedures are known in the art; however, each has its limitations.

The most common method for isolating DNA from whole blood involves the isolation of peripheral blood mononuclear cells (PBMC's) using density gradients. While this method works for research applications, it is generally not suitable for use in a conventional integrated, high throughput microfluidic device.

Hypotonic buffers containing a nonionic detergent can be used to lyse red blood cells (RBC's) as well as white blood cells (WBC's) while leaving the nuclei in tact. In another procedure, only RBC's are lysed when whole blood is subjected to freezing and thawing. The in-tact WBC's or their nuclei can be recovered by centrifugation. For lysis of RBC's without destruction of WBC's, one can also use aqueous dilution as a method. Other methods for selective lysis of RBC's include the use of ammonium chloride or quaternary ammonium salts as well as subjecting RBC's to hypotonic shock in the presence of a hypotonic buffer. However, in conventional methods using one of these approaches, substances that inhibit PCR (e.g., inhibitors of enzymes) are coprecipitated with the nuclei and/or nucleic acid. These inhibitors have to be removed prior to analysis in a conventional high throughput microfluidic device.

While treatment such as boiling, hydrolysis with proteinases, exposure to ultrasonic waves, detergents, or strong bases have been used for the extraction of DNA, alkaline extraction is among the simplest of strategies. For example, U.S. Pat. No. 5,620,852 (Lin et al.) describes an efficient extraction of DNA from whole blood performed with alkaline treatment (e.g., NaOH) at room temperature in a time frame as short as 1 minute. However, in order to get clean DNA, removal of hemoglobin as well as plasma proteins is necessary. This has been accomplished by the use of a brief washing step, for example, by suspension of the blood in water followed by centrifugation, discarding of the supernatant and then extraction of the pellet with NaOH (see, e.g., Biotechniques, Vol. 25, No. 4 (1998) page 588). The large volume of water used to lyse the cells makes the method unsuitable for use in standard microfluidic devices.

U.S. Pat. No. 5,010,183 (Kellogg et al.) describes a centrifugal microfluidics-based platform that uses alkaline lysis for DNA extraction from blood. This method involves mixing a raw sample (e.g., 5 microliters ($\mu$L) of whole blood or an *E. Coli* suspension) with 5 $\mu$L of 10 millimolar (mM) NaOH, heating to 95° C. for 1-2 minutes to lyse cells, releasing DNA and denaturing proteins inhibitory to PCR, neutralizing of the lysate by mixing with 5 $\mu$L of 16 mM TRIS-HCl (pH 7.5), mixing the neutralized lysate with 8-10 $\mu$L of liquid PCR reagents and primers, followed by thermal cycling. Unfortunately, while the reagent volumes are small and suitable for a microfluidic device, downstream processing of DNA in a microfluidic device is challenging.

Another conventional method uses a phenol chloroform extraction. However, this requires the use of toxic and corrosive chemicals and is not easily automated.

Solid phase extraction has also been used for nucleic acid isolation. For example, one method for isolating nucleic acids from a nucleic acid source involves mixing a suspension of silica particles with a buffered chaotropic agent, such as guanidinium thiocyanate, in a reaction vessel followed by addition of the sample. In the presence of the chaotrope, the nucleic acids are adsorbed onto the silica, which is separated from the liquid phase by centrifugation, washed with an alcohol water mix, and finally eluted using a dilute aqueous buffer. Silica solid phase extraction requires the use of the alcohol wash step to remove residual chaotrope without eluting the nucleic acid; however, great care must be taken to remove all traces of the alcohol (by heat evaporation or washing with another very volatile and flammable solvent) in order to prevent inhibition of sensitive enzymes used to amplify or modify the nucleic acid in subsequent steps. The nucleic acid is then eluted with water or an elution buffer. This bind, rinse, and elute procedure is the basis of many commercial kits, such as Qiagen (Valencia, Calif.); however, this procedure is very cumbersome and includes multiple wash steps, making it difficult to adapt to a microfluidic setting.

Ion exchange methods produce high quality nucleic acids. However, ion exchange methods result in the presence of high levels of salts that typically must be removed before the nucleic acids can be further utilized.

International Publication No. WO 01/37291 A1 (MagNA Pure) describes the use of magnetic glass particles and an isolation method in which samples are lysed by incubation with a special buffer containing a chaotropic salt and proteinase K. Glass magnetic particles are added and total nucleic acids contained in the sample are bound to their surface. Unbound substances are removed by several washing steps. Finally, purified total nucleic acid is eluted with a low salt buffer at high temperature.

Yet another conventional method involves applying a biological sample to a hydrophobic organic polymeric solid phase to selectively trap nucleic acid and subsequently remove the trapped nucleic acid with a nonionic surfactant. Another method involves treating a hydrophobic organic polymeric material with a nonionic surfactant, washing the surface, and subsequently contacting the treated solid organic polymeric material with a biological sample to reduce the amount of nucleic acid that binds to the organic polymeric solid phase. Although these solid phase methods are effective methods for isolating nucleic acid from biological samples, other methods are needed, particularly methods that are suitable for use in microfluidic devices.

The discussion of prior publications and other prior knowledge does not constitute an admission that such material was published, known, or part of the common general knowledge.

SUMMARY

The present invention provides methods for the isolation, and preferably purification and recovery, of nucleic acids.

Nucleic acids isolated according to the invention, will be useful, for example, in assays for detection of the presence of a particular nucleic acid in a sample. Such assays are important in the prediction and diagnosis of disease, forensic medicine, epidemiology, and public health. For example, isolated DNA may be subjected to hybridization and/or amplification to detect the presence of an infectious virus or a mutant gene in an individual, allowing determination of the probability that the individual will suffer from a disease of infectious or genetic origin. The ability to detect an infectious virus or a mutation in one sample among the hundreds or thousands of samples being screened takes on substantial importance in the early diagnosis or epidemiology of an at-risk population for disease, e.g., the early detection of HIV infection, cancer or susceptibility to cancer, or in the screening of newborns for diseases, where early detection may be instrumental in diagnosis and treatment. In addition, the methods of the present invention can also be used in basic research laboratories to isolate nucleic acid from cultured cells or biochemical reactions. The nucleic acid can be used for enzymatic modification such as restriction enzyme digestion, sequencing, and amplification.

The present invention provides methods and kits for isolating nucleic acid from a sample that includes nucleic acid (e.g., DNA, RNA, PNA), which may or may not be included within nuclei-containing cells (e.g., white blood cells). These methods involve ultimately separating nucleic acid from inhibitors, such as heme and degradation products thereof (e.g., iron ions or salts thereof), which are undesirable because they can inhibit amplification reactions (e.g., as are used in PCR reactions).

In one embodiment, the present invention provides a method of isolating nucleic acid from a sample, the method including: providing a microfluidic device including a loading chamber, a valved process chamber, and a mixing chamber; providing a sample including nucleic acid and inhibitors; placing the sample in the loading chamber; transferring the sample to the valved process chamber; forming a concentrated region of the sample in the valved process chamber, wherein the concentrated region of the sample includes a majority of the nucleic acid-containing material and the less concentrated region includes at least a portion of the inhibitors; activating a first valve in the valved process chamber to remove at least a portion of the less concentrated region of the sample and substantially separate the concentrated region from the less concentrated region of the sample thereby removing at least a portion of the inhibitors from the sample; activating a second valve in the valved process chamber to transfer the separated concentrated region of the sample to the mixing chamber; optionally diluting the separated concentrated region of the sample with water or buffer, optionally further concentrating the diluted region to increase the concentration of nucleic acid material, optionally separating the further concentrated region, and optionally repeating this process of dilution followed by concentration and separation to reduce the inhibitor concentration to that which would not interfere with an amplification process; optionally lysing nucleic acid-containing material, if present, (with optional heating) to release nucleic acid; and optionally adjusting the pH of the sample including released nucleic acid.

In one embodiment, the present invention provides a method of isolating nucleic acid from a sample, the method including: providing a microfluidic device including a loading chamber, a valved process chamber, and a mixing chamber; providing a sample including nucleic acid-containing material, cells containing inhibitors, and optionally extracellular inhibitors (such nucleic acid-containing material and cells containing inhibitors may be the same or different); placing the sample in the loading chamber; contacting the sample with a first lysing reagent under conditions effective to break cell membranes and release inhibitors and form a lysed sample including nucleic acid-containing material and inhibitors; transferring the lysed sample to the valved process chamber; forming a concentrated region of the lysed sample in the valved process chamber, wherein the concentrated region of the lysed sample includes a majority of the nucleic acid-containing material and the less concentrated region includes at least a portion of the inhibitors; activating a first valve in the valved process chamber to remove at least a portion the less concentrated region of the sample and substantially separate the concentrated region from the less concentrated region of the lysed sample thereby removing at least a portion of the inhibitors from the lysed sample; activating a second valve in the valved process chamber to transfer the separated concentrated region of the lysed sample to the mixing chamber; optionally diluting the separated concentrated region of the lysed sample with water (preferably, RNAse-free sterile water) or buffer, optionally further concentrating the diluted region to increase the concentration of nucleic acid material, optionally separating the further concentrated region, and optionally repeating this process of dilution followed by concentration and separation to reduce the inhibitor concentration to that which would not interfere with an amplification method; further lysing the nucleic acid-containing material to release nucleic acid (with optional heating to denature proteins); and optionally adjusting the pH of the sample including released nucleic acid (and optionally carrying out amplification such as PCR).

In another embodiment, the present invention provides a method of isolating nucleic acid from a sample, the method including: providing a microfluidic device including a loading chamber, a valved process chamber, and a mixing chamber; providing a sample including nucleic acid-containing material, cells containing inhibitors, and optionally extracellular inhibitors (such nucleic acid-containing material and cells containing inhibitors may be the same or different); placing the sample in the loading chamber; contacting the sample with a first lysing reagent under conditions effective to break cell membranes and release inhibitors and form a lysed sample including nucleic acid-containing material and inhibitors; transferring the lysed sample to the valved process chamber; forming a concentrated region of the lysed sample in the valved process chamber, wherein the concentrated region of the lysed sample includes a majority of the nucleic acid-containing material and the less concentrated region includes at least a portion of the inhibitors; activating a first valve in the valved process chamber to remove at least a portion of the less concentrated region of the sample and substantially separate the concentrated region from the less concentrated region of the lysed sample thereby removing at least a portion of the inhibitors from the lysed sample; activating a second valve in the valved process chamber to transfer the separated concentrated region of the lysed sample to the mixing chamber; diluting the separated concentrated region of the lysed sample with water (preferably, RNAse-free sterile water) or buffer, further concentrating the diluted region to increase the concentration of nucleic acid material, separating the further concentrated region, and optionally repeating this process of dilution followed by concentration and separation to reduce the inhibitor concentration to that which would not interfere with an amplification method; further lysing the nucleic acid-containing material with a strong base and heat to release nucleic acid; and adjusting the pH of the sample including released nucleic acid.

The present invention also provides kits for carrying out the various methods of the present invention.

DEFINITIONS

"Nucleic acid" shall have the meaning known in the art and refers to DNA (e.g., genomic DNA, cDNA, or plasmid DNA), RNA (e.g., mRNA, tRNA, or rRNA), and PNA. It can be in a wide variety of forms, including, without limitation, double-stranded or single-stranded configurations, circular form, plasmids, relatively short oligonucleotides, peptide nucleic acids also called PNA's (as described in Nielsen et al., *Chem. Soc. Rev.*, 26, 73-78 (1997)), and the like. The nucleic acid can be genomic DNA, which can include an entire chromosome or a portion of a chromosome. The DNA can include coding (e.g., for coding mRNA, tRNA, and/or rRNA) and/or non-coding sequences (e.g., centromeres, telomeres, intergenic regions, introns, transposons, and/or microsatellite sequences). The nucleic acid can include any of the naturally occurring nucleotides as well as artificial or chemically modified nucleotides, mutated nucleotides, etc. The nucleic acid can include a non-nucleic acid component, e.g., peptides (as in PNA's), labels (radioactive isotopes or fluorescent markers), and the like.

"Nucleic acid-containing material" refers to a source of nucleic acid such as a cell (e.g., white blood cell, enucleated red blood cell), a nuclei, or a virus, or any other composition that houses a structure that includes nucleic acid (e.g., plasmid, cosmid, or viroid, archeobacteriae). The cells can be prokaryotic (e.g., gram positive or gram negative bacteria) or eukaryotic (e.g., blood cell or tissue cell). If the nucleic acid-containing material is a virus, it can include an RNA or a DNA genome; it can be virulent, attenuated, or noninfectious; and it can infect prokaryotic or eukaryotic cells. The nucleic acid-containing material can be naturally occurring, artificially modified, or artificially created.

"Isolated" refers to nucleic acid (or nucleic acid-containing material) that has been separated from at least a portion of the inhibitors (i.e., at least a portion of at least one type of inhibitor) in a sample. This includes separating desired nucleic acid from other materials, e.g., cellular components such as proteins, lipids, salts, and other inhibitors. More preferably, the isolated nucleic acid is substantially purified. "Substantially purified" refers to isolating nucleic acid of at least 3 picogram per microliter (pg/mL), preferably at least 2 nanogram/microliter (ng/μL), and more preferably at least 15 ng/μL, while reducing the inhibitor amount from the original sample by at least 20%, preferably by at least 80% and more preferably by at least 99%. The contaminants are typically cellular components and nuclear components such as heme and related products (hemin, hematin) and metal ions, proteins, lipids, salts, etc., other than the solvent in the sample. Thus, the term "substantially purified" generally refers to separation of a majority of inhibitors (e.g., heme and it degradation products) from the sample, so that compounds capable of interfering with the subsequent use of the isolated nucleic acid are at least partially removed.

"Adheres to" or "adherence" or "binding" refer to reversible retention of inhibitors to an optional solid phase material via a wide variety of mechanisms, including weak forces such as Van der Waals interactions, electrostatic interactions, affinity binding, or physical trapping. The use of this term does not imply a mechanism of action, and includes adsorptive and absorptive mechanisms.

"Solid phase material" (which can optionally be included within a microfluidic device in methods of the present invention) refers to an inorganic or organic material, preferably a polymer made of repeating units, which may be the same or different, of organic and/or inorganic compounds of natural and/or synthetic origin. This includes homopolymers and heteropolymers (e.g., copolymers, terpolymers, tetrapolymers, etc., which may be random or block, for example). This term includes fibrous or particulate forms of a polymer, which can be readily prepared by methods well-known in the art. Such materials typically form a porous matrix, although for certain embodiments, the solid phase also refers to a solid surface, such as a nonporous sheet of polymeric material.

The optional solid phase material may include capture sites. "Capture sites" refer to sites on the solid phase material to which a material adheres. Typically, the capture sites include functional groups or molecules that are either covalently attached or otherwise attached (e.g., hydrophobically attached) to the solid phase material.

The phrase "coating reagent coated on the solid phase material" refers to a material coated on at least a portion of the solid phase material, e.g., on at least a portion of the fibril matrix and/or sorptive particles.

"Surfactant" refers to a substance that lowers the surface or interfacial tension of the medium in which it is dissolved.

"Strong base" refers to a base that is completely dissociated in water, e.g., NaOH.

"Polyelectrolyte" refers to an electrolyte that is a charged polymer, typically of relatively high molecular weight, e.g., polystyrene sulfonic acid.

"Selectively permeable polymeric barrier" refers to a polymeric barrier that allows for selective transport of a fluid based on size and charge.

"Concentrated region" refers to a region of a sample that has a higher concentration of nucleic acid-containing material, nuclei, and/or nucleic acid, which can be in a pellet form, relative to the less concentrated region.

"Substantially separating" as used herein, particularly in the context of separating a concentrated region of a sample from a less concentrated region of a sample, means removing at least 40% of the total amount of nucleic acid (whether it be free, within nuclei, or within other nucleic acid-containing material) in less than 25% of the total volume of the sample. Preferably, at least 75% of the total amount of nucleic acid in less than 10% of the total volume of sample is separated from the remainder of the sample. More preferably, at least 95% of the total amount of nucleic acid in less than 5% of the total volume of sample is separated from the remainder of the sample.

"Inhibitors" refer to inhibitors of enzymes used in amplification reactions, for example. Examples of such inhibitors typically include iron ions or salts thereof (e.g., $Fe^{2+}$ or salts thereof) and other metal salts (e.g., alkali metal ions, transition metal ions). Other inhibitors can include proteins, peptides, lipids, carbohydrates, heme and its degradation products, urea, bile acids, humic acids, polysaccharides, cell membranes, and cytosolic components. The major inhibitors in human blood for PCR are hemoglobin, lactoferrin, and IgG, which are present in erythrocytes, leukocytes, and plasma, respectively. The methods of the present invention separate at least a portion of the inhibitors (i.e., at least a portion of at least one type of inhibitor) from nucleic acid-containing material. As discussed herein, cells containing inhibitors can be the same as the cells containing nuclei or other nucleic acid-containing material. Inhibitors can be contained in cells or be extracellular. Extracellular inhibitors include all inhibitors not contained within cells, which includes those inhibitors present in serum or viruses, for example.

"Preferentially adhere at least a portion of the inhibitors to the solid phase material" means that one or more types of inhibitors will adhere to the optional solid phase material to a greater extent than nucleic acid-containing material (e.g., nuclei) and/or nucleic acid, and typically without adhering a substantial portion of the nucleic acid-containing material and/or nuclei to the solid phase material.

"Microfluidic" refers to a device with one or more fluid passages, chambers, or conduits that have at least one internal cross-sectional dimension, e.g., depth, width, length, diameter, etc., that is less than 500 µm, and typically between 0.1 µm and 500 µm. In the devices used in the present invention, the microscale channels or chambers preferably have at least one cross-sectional dimension between 0.1 µm and 200 µm, more preferably between 0.1 µm and 100 µm, and often between 1 µm and 20 µm. Typically, a microfluidic device includes a plurality of chambers (process chambers, separation chambers, mixing chambers, waste chambers, diluting reagent chambers, amplification reaction chambers, loading chambers, and the like), each of the chambers defining a volume for containing a sample; and at least one distribution channel connecting the plurality of chambers of the array; wherein at least one of the chambers within the array can include a lysing reagent (thereby often being referred to as a mixing chamber).

The terms "comprises" and variations thereof do not have a limiting meaning where these terms appear in the description and claims.

As used herein, "a," "an," "the," "at least one," and "one or more" are used interchangeably and mean one or more.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list. Furthermore, various embodiments are described in which the various elements of each embodiment could be used in other embodiments, even though not specifically described.

DETAILED DESCRIPTION OF ILLUSTRATIVE EMBODIMENTS

Figure 1:
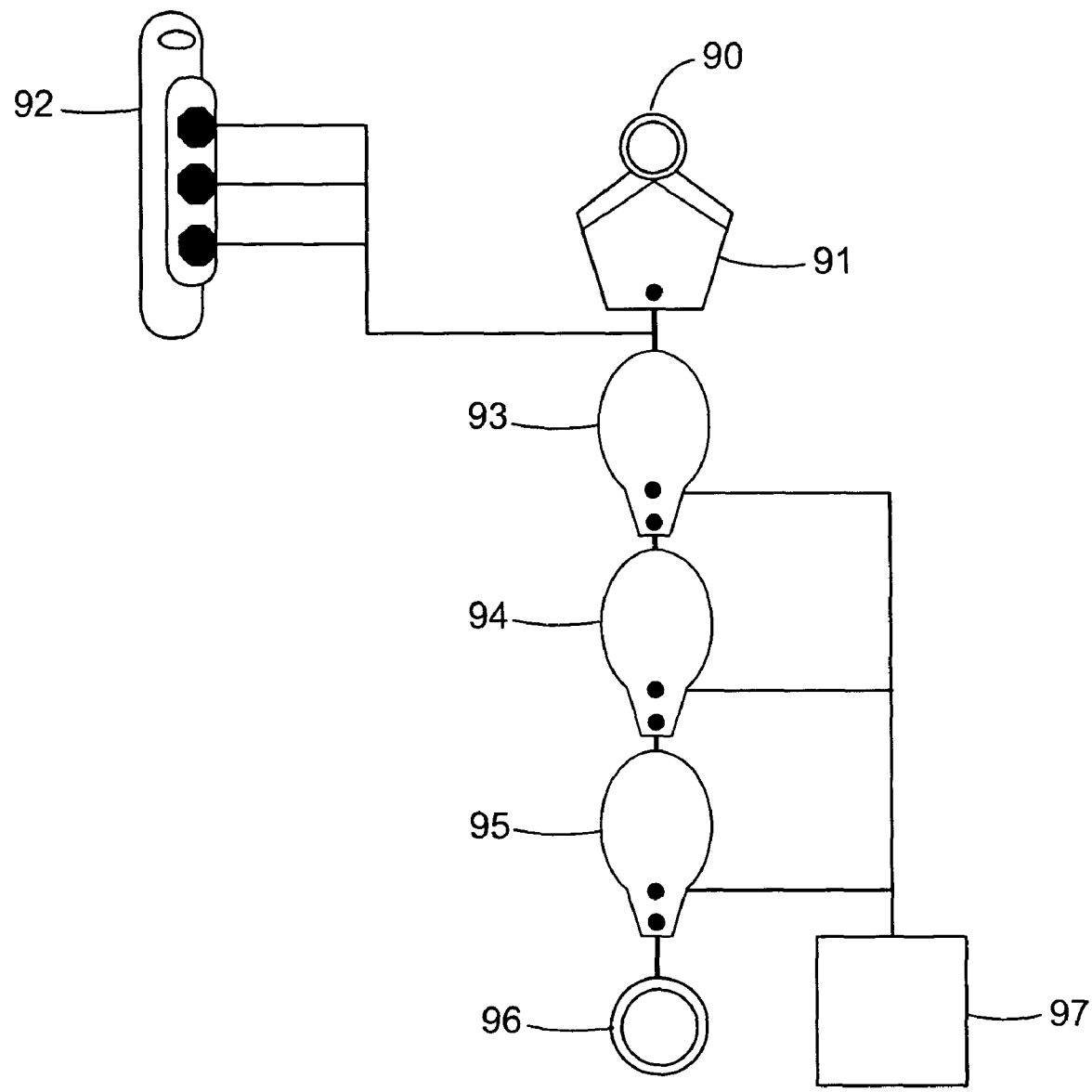
FIG. 1 is a representation of a microfluidic device used in certain methods of the present invention.

The present invention provides various methods and kits for isolating nucleic acid from a sample, typically a biological sample, preferably in a substantially purified form. The present invention provides methods and kits for isolating nucleic acid from a sample that includes nucleic acid (e.g., DNA, RNA, PNA), which may or may not be included within nuclei-containing cells (e.g., white blood cells).

It should be understood that although the methods are directed to isolating nucleic acid from a sample, the methods do not necessarily remove the nucleic acid from the nucleic acid-containing material (e.g., nuclei). That is, further steps may be required to further separate the nucleic acid from the nuclei, for example.

The methods of the present invention involve ultimately separating nucleic acid from inhibitors, such as heme and degradation products thereof (e.g., iron salts), which are undesirable because they can inhibit amplification reactions (e.g., as are used in PCR reactions). More specifically, the methods of the present invention involve separating at least a portion of the nucleic acid in a sample from at least a portion of at least one type of inhibitor. Preferred methods involve removing substantially all the inhibitors in a sample containing nucleic acid such that the nucleic acid is substantially pure. For example, the final concentration of iron-containing inhibitors is no greater than about 0.8 micromolar (µM), which is the current level tolerated in conventional PCR systems.

In order to get clean DNA from whole blood, removal of hemoglobin as well as plasma proteins is typically desired. When red blood cells are lysed, heme and related compounds are released that inhibit Taq Polymerase. The normal hemoglobin concentration in whole blood is 15 grams (g) per 100 milliliters (mL) based on which the concentration of heme in hemolysed whole blood is around 10 millimolar (mM). For PCR to work out satisfactorily, the concentration of heme should be reduced to the micromolar (µM) level. This can be achieved by dilution or by removal of inhibitors using a material that binds inhibitors, for example.

Typically, a sample containing nucleic acid is processed in a flow-through receptacle, although this receptacle is not a necessary requirement of the present invention. Preferably, for certain methods of the present invention, the processing equipment is in a microfluidic format.

Samples

The methods of the present invention can be used to isolate nucleic acids from a wide variety of samples, particularly biological samples, such as body fluids (e.g., whole blood, blood serum, urine, saliva, cerebral spinal fluid, semen, or synovial lymphatic fluid), various tissues (e.g., skin, hair, fur, feces, tumors, or organs such as liver or spleen), cell cultures or cell culture supernatants, etc. The sample can be a food sample, a beverage sample, a fermentation broth, a clinical sample used to diagnose, treat, monitor, or cure a disease or disorder, a forensic sample, an agricultural sample (e.g., from a plant or animal), or an environmental sample (e.g., soil, dirt, or garbage).

Biological samples are those of biological or biochemical origin. Those suitable for use in the methods of the present invention can be derived from mammalian, plant, bacterial, or yeast sources. The biological sample can be in the form of single cells or in the form of a tissue. Cells or tissue can be derived from in vitro culture. Significantly, certain embodiments of the invention use whole blood without any preprocessing (e.g., lysing, filtering, etc.) as the sample of interest.

For certain embodiments, a sample such as whole blood can be preprocessed by centrifuging and the white blood cells (i.e., the buffy coat) separated from the blood and used as the sample in the methods of the invention.

For certain embodiments, a sample can be subjected to ultracentrifugation to concentrate the sample prior to subjecting it to a process of the present invention (i.e., prior to adding the sample to a microfluidic device). This is particularly desirable for virus-containing samples.

The sample can be a solid sample (e.g., solid tissue) that is dissolved or dispersed in water or an organic medium, or from which the nucleic acid has been extracted into water or an organic medium. For example, the sample can be an organ homogenate (e.g., liver, spleen). Thus, the sample can include previously extracted nucleic acid (particularly if it is a solid sample).

The type of sample is not a limitation of the present invention. Typically, however, the sample will include nucleic acid-containing material and inhibitors from which the nucleic acid needs to be separated. In this context, nucleic acid-containing material refers to cells (e.g., white blood cell, bacterial cells), nuclei, viruses, or any other composition that houses a structure that includes nucleic acid (e.g., plasmid, cosmid, or viroid, archeobacteriae). In certain preferred embodiments of such methods, the nucleic acid-containing material includes nuclei. In certain embodiments, such nuclei are in-tact (i.e., substantially unlysed).

In certain embodiments, the sample may be partially lysed (e.g., pre-lysed to release inhibitors), in which case lysing may be required in the process of the present invention. In certain embodiments, the sample may be completely lysed, in which case no lysing reagent is necessarily needed in the process of the present invention. Thus, a sample can include free (e.g., not within cells) nucleic acid and free (e.g., not within cells) inhibitors).

The isolated (i.e., separated from inhibitors) nucleic acid can be used, preferably without further purification or washing, for a wide variety of applications (e.g., amplification, sequencing, labeling, annealing, restriction digest, ligation, reverse transcriptase, hybridization, Southern blot, Northern blot, etc.). In particularly, it can be used for determining a subject's genome. It can be used for the diagnosis of the presence of a microorganism (e.g., bacteria, virus) in a sample, and subsequently can be used for monitoring and/or remedying the damage caused by the microorganism to the source of the sample. The methods, materials, systems, and kits of the present invention are especially well-suited for preparing nucleic acid extracts for use in amplification techniques (e.g., PCR, LCR, MASBA, SDA, and bDNA) used in high throughput or automated processes, particularly microfluidic systems. Thus, for certain embodiments of the present invention, the isolated nucleic acid is transferred to an amplification reaction chamber (such as a PCR sample chamber in a microfluidic device).

The nucleic acids may be isolated (i.e., separated from inhibitors) according to the invention from an impure, partially pure, or a pure sample. The purity of the original sample is not critical, as nucleic acid may be isolated from even grossly impure samples. For example, nucleic acid may be obtained from an impure sample of a biological fluid such as blood, saliva, or tissue. If an original sample of higher purity is desired, the sample may be treated according to any conventional means known to those of skill in the art prior to undergoing the methods of the present invention. For example, the sample may be processed so as to remove certain impurities such as insoluble materials prior to subjecting the sample to a method of the present invention.

The nucleic acid isolated as described herein may be of any molecular weight and in single-stranded form, double-stranded form, circular, plasmid, etc. Various types of nucleic acid can be separated from each other (e.g., RNA from DNA, or double-stranded DNA from single-stranded DNA). For example, small oligonucleotides or nucleic acid molecules of about 10 to about 50 bases in length, much longer molecules of about 1000 bases to about 10,000 bases in length, and even high molecular weight nucleic acids of about 50 kb to about 500 kb can be isolated using the methods of the present invention. In some aspects, a nucleic acid isolated according to the invention may preferably be in the range of about 10 bases to about 100 kilobases.

The nucleic acid-containing sample may be in a wide variety of volumes. For example, for a microfluidic format, typically very small volumes, e.g., 10 µL (and preferably, no greater than 100 µL) are preferred. It should be understood that larger samples can be used if preprocessed, such as by concentrating.

For low copy number genes, one typically would need a larger sample size to ensure that the sequence of interest is present in the sample. Larger sample sizes, however, have a greater amount of inhibitors and do not typically lend themselves to a microfluidic format. Thus, for a low copy number situation, it may be necessary to use a 100 µL or higher volume in order to get a reproducible result; however, the number of samples processed per microfluidic device may be reduced due to the higher sample volume.

In the methods of the present invention, a centrifugation step to concentrate nucleic acid-containing material is useful for low copy number samples. However, while the nucleic acid concentration is increased substantially at the bottom of the process chamber, for example, the inhibitor concentration is still high. While most of the inhibitors, the proteins in the serum and the broken RBC's (e.g., heme and heme-related products) are removed in the less concentrated region, the nucleic acid-containing concentrated region of the sample still has a significant amount of inhibitor present; however, the ratio of nucleic acid to that of the inhibitor is very high, resulting in an enriched sample with respect to nucleic acid. This concentrated region of the sample can then be contacted with an optional solid phase material, as described herein, to remove residual inhibitors, if desired.

For high copy number genes, a sample size as small as 2 µL can be used, but reproducibility is better with larger volumes (e.g., 20 µL). In the case of smaller volumes, higher throughputs (i.e., number of samples processed per microfluidic device) can be obtained. In the case of larger volumes (e.g., 20 µL), it may not be necessary to go through a pre-spin step for concentration of nucleic acid-containing cells.

For those embodiments in which a solid phase material is used in addition to the concentration/separation process described herein, the nucleic acid-containing sample applied to the solid phase material may be any amount, that amount being determined by the amount of the solid phase material. Preferably, the amount of nucleic acid in a sample applied to the solid phase material is less than the dried weight of the solid phase material, typically about 1/10,000 to about 1/100 (weight nucleic acid/solid phase). The amount of nucleic acid in a sample applied to the optional solid phase material may be as much as 100 grams or as little as 1 picogram, for example.

The desired nucleic acid isolated from the methods of the present invention is preferably in an amount of at least 20%, more preferably in an amount of at least 30%, more preferably at least 70%, and most preferably at least 90%, of the amount of total nucleic acid in the originally applied sample. Thus, certain preferred methods of the present invention provide for high recovery of the desired nucleic acid from a sample. Furthermore, exceedingly small amounts of nucleic acid molecules may be quantitatively recovered according to the invention. The recovery or yield is mainly dependent on the quality of the sample rather than the procedure itself. Because certain embodiments of the invention provide a nucleic acid preparation that does not require concentration from a large volume, the invention avoids risk of loss of the nucleic acid.

Having too much DNA in a PCR sample can be detrimental to amplification of DNA as there are a lot of misprimed sites. This results in a large number of linearly or exponentially amplified non-target sequences. Since the specificity of the amplification is lost as the amount of non-target DNA is increased, the exponential accumulation of the target sequence of interest does not occur to any significant degree. Thus, it is desirable to control the amount of DNA that goes into each PCR sample. The DNA amount is typically not more than 1 microgram/reaction, typically at least 1 picogram/reaction. The typical final DNA concentration in a PCR mixture ranges from 0.15 nanogram/microliter to 1.5 nanograms/microliter. In the case of a microfluidic device, a sample can be split after clean-up, prior to PCR, such that each sample has the right amount of DNA. Alternatively, a sample can be diluted sufficiently in a sample processing device (particularly, a microfluidic device) that includes a variable valved process chamber, described in greater detail below, so that the right amount of DNA is present in each PCR mixture. In a diagnostic setting, since the amount of white blood cells can vary significantly, it is hard to apriori predict the amount of DNA that will be isolated. However, a useful range is 3 micrograms (μg) to 12 μg of DNA per 200 μL of blood. For buffy coats, 25 μg to 50 μg per 200 μL of buffy coat is a useful range.

Lysing Reagents and Conditions

For certain embodiments of the invention, at some point during the process, cells within the sample, particularly nucleic acid-containing cells (e.g., white blood cells, bacterial cells, viral cells) are lysed to release the contents of the cells and form a sample (i.e., a lysate). Lysis herein is the physical disruption of the membranes of the cells, referring to the outer cell membrane and, when present, the nuclear membrane. This can be done using standard techniques, such as by hydrolyzing with proteinases followed by heat inactivation of proteinases, treating with surfactants (e.g., nonionic surfactants or sodium dodecyl sulfate), guanidinium salts, or strong bases (e.g., NaOH), disrupting physically (e.g., with ultrasonic waves), boiling, or heating/cooling (e.g., heating to at least 55° C. (typically to 95° C.) and cooling to room temperature or below (typically to 8° C.)), which can include a freezing/thawing process. Typically, if a lysing reagent is used, it is in aqueous media, although organic solvents can be used, if desired.

Lysing of red blood cells (RBC's) without the destruction of white blood cells (WBC's) in whole blood can occur to release inhibitors through the use of water (i.e., aqueous dilution) as the lysing agent (i.e., lysing reagent). Alternatively, ammonium chloride or quaternary ammonium salts can also be used to break RBC's. The RBC's can also be lysed by hypotonic shock with the use of a hypotonic buffer. The in-tact (i.e., unbroken) WBC's or their nuclei can be recovered by centrifugation, for example.

Typically, a stronger lysing reagent, such as a surfactant, can be used to lyse RBC's as well as nucleic acid-containing cells (e.g., white blood cells (WBC's), bacterial cells, viral cells) to release inhibitors, nuclei, and/or nucleic acid. For example, a nonionic surfactant can be used to lyse RBC's as well as WBC's while leaving the nuclei in tact. Nonionic surfactants, cationic surfactants, anionic surfactants, and zwitterionic surfactants can be used to lyse cells. Particularly useful are nonionic surfactants. Combinations of surfactants can be used if desired. A nonionic surfactant such as TRITON X-100 can be added to a TRIS buffer containing sucrose and magnesium salts for isolation of nuclei.

The amount of surfactant used for lysing is sufficiently high to effectively lyse the sample, yet sufficiently low to avoid precipitation, for example. The concentration of surfactant used in lysing procedures is typically at least 0.1 wt-%, based on the total weight of the sample. The concentration of surfactant used in lysing procedures is typically no greater than 4.0 wt-%, and preferably, no greater than 1.0 wt-%, based on the total weight of the sample. The concentration is usually optimized in order to obtain complete lysis in the shortest possible time with the resulting mixture being PCR compatible. In fact, the nucleic acid in the formulation added to the PCR cocktail should allow for little or no inhibition of real-time PCR.

If desired, a buffer can be used in admixture with the surfactant. Typically, such buffers provide the sample with a pH of at least 7, and typically no more than 9.

Typically, an even stronger lysing reagent, such as a strong base, can be used to lyse any nuclei contained in the nucleic acid-containing cells (as in white blood cells) to release nucleic acid. For example, the method described in U.S. Pat. No. 5,620,852 (Lin et al.), which involves extraction of DNA from whole blood with alkaline treatment (e.g., NaOH) at room temperature in a time frame as short as 1 minute, can be adapted to certain methods of the present invention. Generally, a wide variety of strong bases can be used to create an effective pH (e.g., 8-13, preferably 13) in an alkaline lysis procedure. The strong base is typically a hydroxide such as NaOH, LiOH, KOH; hydroxides with quaternary nitrogen-containing cations (e.g., quaternary ammonium) as well as bases such as tertiary, secondary or primary amines. Typically, the concentration of the strong base is at least 0.01 Normal (N), and typically, no more than 1 N. Typically, the mixture can then be neutralized, particularly if the nucleic acid is subjected to PCR. In another procedure, heating can be used subsequent to lysing with base to further denature proteins followed by neutralizing the sample.

One can also use Proteinase K with heat followed by heat inactivation of proteinase K at higher temperatures for isolation of nucleic acids from the nuclei or WBC.

One can also use a commercially available lysing agent and neutralization agent such as in Sigma's Extract-N-Amp Blood PCR kit scaled down to microfluidic dimensions. Stonger lysing solutions such as POWERLYSE from GenPoint (Oslo, Norway) for lysing difficult bacteria such as *Staphylococcus, Streptococcus*, etc. can be used to advantage in certain methods of the present invention.

In another procedure, a boiling method can be used to lyse cells and nuclei, release DNA, and precipitate hemoglobin simultaneously. The DNA in the supernatant can be used directly for PCR without a concentration step, making this procedure useful for low copy number samples.

In another procedure, heating can be used subsequent to lysing with base to further denature proteins followed by neutralizing the sample.

For infectious diseases, it may be necessary to analyze bacterial or viruses from whole blood. For example, in the case of bacteria, white blood cells may be present in conjunction with bacterial cells. In a microfluidic device, it would be possible to lyse red blood cells to release inhibitors, and then separate out bacterial cells and white blood cells by centrifugation, for example, prior to further lysing. This concentrated slug of nucleic acid-containing cells (bacterial and white blood cells/nuclei) can be moved further into a chamber for removal of inhibitors. Then, the bacterial cells, for example, can be lysed.

Bacterial cell lysis, depending on the type, may be accomplished using heat. Alternatively, bacterial cell lysis can occur using enzymatic methods (e.g., lysozyme, mutanolysin) or chemical methods. The bacterial cells are preferably lysed by alkaline lysis.

The use of bacteria for propagation of plasmids is common in the study of genomics, analytic molecular biology, preparatory molecular biology, etc. In the case of the bacterium containing plasmid, genetic material from both the bacterium and the plasmid are present. A clean-up procedure to separate cellular proteins and cellular fragments from genomic DNA can be carried out using a method of the present invention. The supernatant thus obtained, which contains the plasmid DNA, is called the "cleared lysate." The cleared lysate can be further purified using a variety of means, such as anion-exchange chromatography, gel filtration, or precipitation with alcohol.

In a specific example of a protocol for bacterial cultures, which can be incorporated into a microfluidic device, an *E. Coli* cell culture is centrifuged and resuspended in TE buffer (10 mM TRIS, 1 mM EDTA, pH 7.5) and lysed by the addition of 0.1 M NaOH/1% SDS (sodium dodecyl sulfate). The cell lysis is stopped by the addition of 1 volume of 3 M (three molar) potassium acetate (pH 4.8) and the supernatant centrifuged. The cell lysate is further purified to get clean plasmid DNA.

Plasma and serum represent the majority of specimens submitted for molecular testing that include viruses. After fractionation of whole blood, plasma or serum samples can be used for the extraction of viruses (i.e., viral particles). For example, to isolate DNA from viruses, it is possible to first separate out the serum by spinning blood. By the use of the variable valve, which is described in greater detail below, the serum alone can be emptied into another chamber. The serum can then be centrifuged to concentrate the virus or can be used directly in subsequent lysis steps after removal of the inhibitors using an optional solid phase material, for example, as described herein. The solid phase material could absorb the solution such that the virus particles do not go through the material. The virus particles can then be eluted out in a small elution volume. The virus can be lysed by heat or by enzymatic or chemical means, for example, by the use of surfactants, and used for downstream applications, such as PCR or real-time PCR. In cases where viral RNA is required, it may be necessary to have an RNAse inhibitor added to the solution to prevent degradation of RNA.

Optional Solid Phase Material

For certain embodiments of the invention, it has been found that inhibitors will adhere to solid phase (preferably polymeric) materials that include a solid matrix in any form (e.g., particles, fibrils, a membrane), preferably with capture sites (e.g., chelating functional groups) attached thereto, a coating reagent (preferably, surfactant) coated on the solid phase material, or both. The coating reagent can be a cationic, anionic, nonionic, or zwitterionic surfactant. Alternatively, the coating reagent can be a polyelectrolyte or a strong base. Various combinations of coating reagents can be used if desired.

The solid phase material useful in the methods of the present invention may include a wide variety of organic and/or inorganic materials that retain inhibitors such as heme and heme degradation products, particularly iron ions, for example. Such materials are functionalized with capture sites (preferably, chelating groups), coated with one or more coating reagents (e.g., surfactants, polyelectrolytes, or strong bases), or both. Typically, the solid phase material includes an organic polymeric matrix.

Generally suitable materials are chemically inert, physically and chemically stable, and compatible with a variety of biological samples. Examples of solid phase materials include silica, zirconia, alumina beads, metal colloids such as gold, gold coated sheets that have been functionalized through mercapto chemistry, for example, to generate capture sites. Examples of suitable polymers include for example, polyolefins and fluorinated polymers. The solid phase material is typically washed to remove salts and other contaminants prior to use. It can either be stored dry or in aqueous suspension ready for use. The solid phase material is preferably used in a flow-through receptacle, for example, such as a pipet, syringe, or larger column, microtiter plate, or microfluidic device, although suspension methods that do not involve such receptacles could also be used.

The solid phase material useful in the methods of the present invention can include a wide variety of materials in a wide variety of forms. For example, it can be in the form of particles or beads, which may be loose or immobilized, fibers, foams, frits, microporous film, membrane, or a substrate with microreplicated surface(s). If the solid phase material includes particles, they are preferably uniform, spherical, and rigid to ensure good fluid flow characteristics.

For flow-through applications of the present invention, such materials are typically in the form of a loose, porous network to allow uniform and unimpaired entry and exit of large molecules and to provide a large surface area. Preferably, for such applications, the solid phase material has a relatively high surface area, such as, for example, more than one meter squared per gram ($m^2/g$). For applications that do not involve the use of a flow-through device, the solid phase material may or may not be in a porous matrix. Thus, membranes can also be useful in certain methods of the present invention.

For applications that use particles or beads, they may be introduced to the sample or the sample introduced into a bed of particles/beads and removed therefrom by centrifuging, for example. Alternatively, particles/beads can be coated (e.g., pattern coated) onto an inert substrate (e.g., polycarbonate or polyethylene), optionally coated with an adhesive, by a variety of methods (e.g., spray drying). If desired, the substrate can be microreplicated for increased surface area and enhanced clean-up. It can also be pretreated with oxygen plasma, e-beam or ultraviolet radiation, heat, or a corona treatment process. This substrate can be used, for example, as a cover film, or laminated to a cover film, on a reservoir in a microfluidic device.

In one embodiment, the solid phase material includes a fibril matrix, which may or may not have particles enmeshed therein. The fibril matrix can include any of a wide variety of fibers. Typically, the fibers are insoluble in an aqueous environment. Examples include glass fibers, polyolefin fibers, particularly polypropylene and polyethylene microfibers, aramid fibers, a fluorinated polymer, particularly, polytetrafluoroethylene fibers, and natural cellulosic fibers. Mixtures of fibers can be used, which may be active or inactive toward binding of nucleic acid. Preferably, the fibril matrix forms a web that is at least about 15 microns, and no greater than about 1 millimeter, and more preferably, no greater than about 500 microns thick.

If used, the particles are typically insoluble in an aqueous environment. They can be made of one material or a combination of materials, such as in a coated particle. They can be swellable or nonswellable, although they are preferably nonswellable in water and organic liquids. Preferably, if the particle is doing the adhering, it is made of nonswelling, hydrophobic material. They can be chosen for their affinity for the nucleic acid. Examples of some water swellable particles are described in U.S. Pat. Nos. 4,565,663 (Errede et al.), 4,460,642 (Errede et al.), and 4,373,519 (Errede et al.). Particles that are nonswellable in water are described in U.S. Pat. Nos. 4,810,381 (Hagen et al.), 4,906,378 (Hagen et al.), 4,971,736 (Hagen et al.); and 5,279,742 (Markell et al.). Preferred particles are polyolefin particles, such as polypropylene particles (e.g., powder). Mixtures of particles can be used, which may be active or inactive toward binding of nucleic acid.

If coated particles are used, the coating is preferably an aqueous- or organic-insoluble, nonswellable material. The coating may or may not be one to which nucleic acid will adhere. Thus, the base particle that is coated can be inorganic or organic. The base particles can include inorganic oxides such as silica, alumina, titania, zirconia, etc., to which are covalently bonded organic groups. For example, covalently bonded organic groups such as aliphatic groups of varying chain length (C2, C4, C8, or C18 groups) can be used.

Examples of suitable solid phase materials that include a fibril matrix are described in U.S. Pat. Nos. 5,279,742 (Markell et al.), 4,906,378 (Hagen et al.), 4,153,661 (Ree et al.), 5,071,610 (Hagen et al.), 5,147,539 (Hagen et al.), 5,207,915 (Hagen et al.), and 5,238,621 (Hagen et al.). Such materials are commercially available from 3M Company (St. Paul, Minn.) under the trade designations SDB-RPS (Styrene-Divinyl Benzene Reverse Phase Sulfonate, 3M Part No. 2241), cation-SR membrane (3M Part No. 2251), C-8 membrane (3M Part No. 2214), and anion-SR membrane (3M Part No. 2252).

Those that include a polytetrafluoroethylene matrix (PTFE) are particularly preferred. For example, U.S. Pat. No. 4,810,381 (Hagen et al.) discloses a solid phase material that includes: a polytetrafluoroethylene fibril matrix, and non-swellable sorptive particles enmeshed in the matrix, wherein the ratio of nonswellable sorptive particles to polytetrafluoroethylene being in the range of 19:1 to 4:1 by weight, and further wherein the composite solid phase material has a net surface energy in the range of 20 to 300 milliNewtons per meter. U.S. Pat. No. RE 36,811 (Markell et al.) discloses a solid phase extraction medium that includes: a PTFE fibril matrix, and sorptive particles enmeshed in the matrix, wherein the particles include more than 30 and up to 100 weight percent of porous organic particles, and less than 70 to 0 weight percent of porous (organic-coated or uncoated) inorganic particles, the ratio of sorptive particles to PTFE being in the range of 40:1 to 1:4 by weight.

Particularly preferred solid phase materials are available under the trade designation EMPORE from the 3M Company, St. Paul, Minn. The fundamental basis of the EMPORE technology is the ability to create a particle-loaded membrane, or disk, using any sorbent particle. The particles are tightly held together within an inert matrix of polytetrafluoroethylene (90% sorbent: 10% PTFE, by weight). The PTFE fibrils do not interfere with the activity of the particles in any way. The EMPORE membrane fabrication process results in a denser, more uniform extraction medium than can be achieved in a traditional Solid Phase Extraction (SPE) column or cartridge prepared with the same size particles.

In another preferred embodiment, the solid phase (e.g., a microporous thermoplastic polymeric support) has a microporous structure characterized by a multiplicity of spaced, randomly dispersed, nonuniform shaped, equiaxed particles of thermoplastic polymer connected by fibrils. Particles are spaced from one another to provide a network of micropores therebetween. Particles are connected to each other by fibrils, which radiate from each particle to the adjacent particles. Either, or both, the particles or fibrils may be hydrophobic. Examples of preferred such materials have a high surface area, often as high as 40 meters$^2$/gram as measured by Hg surface area techniques and pore sizes up to about 5 microns.

This type of fibrous material can be made by a preferred technique that involves the use of induced phase separation. This involves melt blending a thermoplastic polymer with an immiscible liquid at a temperature sufficient to form a homogeneous mixture, forming an article from the solution into the desired shape, cooling the shaped article so as to induce phase separation of the liquid and the polymer, and to ultimately solidify the polymer and remove a substantial portion of the liquid leaving a microporous polymer matrix. This method and the preferred materials are described in detail in U.S. Pat. Nos. 4,726,989 (Mrozinski), 4,957,943 (McAllister et al.), and 4,539,256 (Shipman). Such materials are referred to as thermally induced phase separation membranes (TIPS membranes) and are particularly preferred.

Other suitable solid phase materials include nonwoven materials as disclosed in U.S. Pat. No. 5,328,758 (Markell et al.). This material includes a compressed or fused particulate-containing nonwoven web (preferably blown microfibrous) that includes high sorptive-efficiency chromatographic grade particles.

Other suitable solid phase materials include those known as HIPE Foams, which are described, for example, in U.S. patent Publication Ser. No. 2003/0011092 (Tan et al.). "HIPE" or "high internal phase emulsion" means an emulsion that includes a continuous reactive phase, typically an oil phase, and a discontinuous or co-continuous phase immiscible with the oil phase, typically a water phase, wherein the immiscible phase includes at least 74 volume percent of the emulsion. Many polymeric foams made from HIPE's are typically relatively open-celled. This means that most or all of the cells are in unobstructed communication with adjoining cells. The cells in such substantially open-celled foam structures have intercellular windows that are typically large enough to permit fluid transfer from one cell to another within the foam structure.

The solid phase material can include capture sites for inhibitors. Herein, "capture sites" refer to groups that are either covalently attached (e.g., functional groups) or molecules that are noncovalently (e.g., hydrophobically) attached to the solid phase material.

Preferably, the solid phase material includes functional groups that capture the inhibitors. For example, the solid phase material may include chelating groups. In this context, "chelating groups" are those that are polydentate and capable of forming a chelation complex with a metal atom or ion (although the inhibitors may or may not be retained on the solid phase material through a chelation mechanism). The incorporation of chelating groups can be accomplished through a variety of techniques. For example, a nonwoven material can hold beads functionalized with chelating groups. Alternatively, the fibers of the nonwoven material can be directly functionalized with chelating groups.

Examples of chelating groups include, for example, —$(CH_2—C(O)OH)_2$, tris(2-aminoethyl)amine groups, iminodiacetic acid groups, nitrilotriacetic acid groups. The chelating groups can be incorporated into a solid phase material through a variety of techniques. They can be incorporated in by chemically synthesizing the material. Alternatively, a polymer containing the desired chelating groups can be coated (e.g., pattern coated) on an inert substrate (e.g., polycarbonate or polyethylene). If desired, the substrate can be microreplicated for increased surface area and enhanced clean-up. It can also be pretreated with oxygen plasma, e-beam or ultraviolet radiation, heat, or a corona treatment process. This substrate can be used, for example, as a cover film, or laminated to a cover film, on a reservoir in a microfluidic device.

Chelating solid phase materials are commercially available and could be used as the solid phase material in the present invention. For example, for certain embodiments of the present invention, EMPORE membranes that include chelating groups such as iminodiacetic acid (in the form of the sodium salt) are preferred. Examples of such membranes are disclosed in U.S. Pat. No. 5,147,539 (Hagen et al.) and commercially available as EMPORE Extraction Disks (47 mm, No. 2271 or 90 mm, No. 2371) from the 3M Company. For certain embodiments of the present invention, ammonium-derivatized EMPORE membranes that include chelating groups are preferred. To put the disk in the ammonium form, it can be washed with 50 mL of 0.1M ammonium acetate buffer at pH 5.3 followed with several reagent water washes.

Examples of other chelating materials include, but are not limited to, crosslinked polystyrene beads available under the trade designation CHELEX from Bio-Rad Laboratories, Inc. (Hercules, Calif.), crosslinked agarose beads with tris(2-aminoethyl)amine, iminodiacetic acid, nitrilotriacetic acid, polyamines and polyimines as well as the chelating ion exchange resins commercially available under the trade designation DUOLITE C-467 and DUOLITE GT73 from Rohm and Haas (Philadelphia, Pa.), AMBERLITE IRC-748, DIAION CR11, DUOLITE C647.

Typically, a desired concentration density of chelating groups on the solid phase material is about 0.02 nanomole per millimeter squared, although it is believed that a wider range of concentration densities is possible.

Other types of capture materials include anion exchange materials, cation exchange materials, activated carbon, reverse phase, normal phase, styrene-divinyl benzene, alumina, silica, zirconia, and metal colloids. Examples of suitable anion exchange materials include strong anion exchangers such as quaternary ammonium, dimethylethanolamine, quaternary alkylamine, trimethylbenzyl ammonium, and dimethylethanolbenzyl ammonium usually in the chloride form, and weak anion exchangers such as polyamine. Examples of suitable cation exchange materials include strong cation exchangers such as sulfonic acid typically in the sodium form, and weak cation exchangers such as carboxylic acid typically in the hydrogen form. Examples of suitable carbon-based materials include EMPORE carbon materials, carbon beads, Examples of suitable reverse phase C8 and C18 materials include silica beads that are end-capped with octadecyl groups or octyl groups and EMPORE materials that have C8 and C18 silica beads (EMPORE materials are available from 3M Co., St. Paul, Minn.). Examples of normal phase materials include hydroxy groups and dihydroxy groups.

Commercially available materials can also be modified or directly used in methods of the present invention. For example, solid phase materials available under the trade designation LYSE AND GO (Pierce, Rockford, Ill.), RELEASE-IT (CPG, NJ), GENE FIZZ (Eurobio, France), GENE RELEASER (Bioventures Inc., Murfreesboro, Tenn.), and BUGS N BEADS (GenPoint, Oslo, Norway), as well as Zymo's beads (Zymo Research, Orange, Calif.) and Dynal's beads (Dynal, Oslo, Norway) can be incorporated into the methods of the present invention, particularly into a microfluidic device as the solid phase capture material.

In certain embodiments of such methods, the solid phase material includes a coating reagent. The coating reagent is preferably selected from the group consisting of a surfactant, a strong base, a polyelectrolyte, a selectively permeable polymeric barrier, and combinations thereof. In certain embodiments of such methods, the solid phase material includes a polytetrafluoroethylene fibril matrix, sorptive particles enmeshed in the matrix, and a coating reagent coated on the solid phase material, wherein the coating reagent is selected from the group consisting of a surfactant, a strong base, a polyelectrolyte, a selectively permeable polymeric barrier, and combinations thereof. Herein, the phrase "coating reagent coated on the solid phase material" refers to a material coated on at least a portion of the solid phase material, e.g., on at least a portion of the fibril matrix and/or sorptive particles.

Examples of suitable surfactants are listed below.

Examples of suitable strong bases include NaOH, KOH, LiOH, NH$_4$OH, as well as primary, secondary, or tertiary amines.

Examples of suitable polyelectrolytes include, polystryene sulfonic acid (e.g., poly(sodium 4-styrenesulfonate) or PSSA), polyvinyl phosphonic acid, polyvinyl boric acid, polyvinyl sulfonic acid, polyvinyl sulfuric acid, polystyrene phosphonic acid, polyacrylic acid, polymethacrylic acid, lignosulfonate, carrageenan, heparin, chondritin sulfate, and salts or other derivatives thereof.

Examples of suitable selectively permeable polymeric barriers include polymers such as acrylates, acryl amides, azlactones, polyvinyl alcohol, polyethylene imine, polysaccharides. Such polymers can be in a variety of forms. They can be water-soluble, water-swellable, water-insoluble, hydrogels, etc. For example, a polymeric barrier can be prepared such that it acts as a filter for larger particles such as white blood cells, nuclei, viruses, bacteria, as well as nucleic acids such as human genomic DNA and proteins. These surfaces could be tailored by one of skill in the art to separate on the basis of size and/or charge by appropriate selection of functional groups, by cross-linking, and the like. Such materials would be readily available or prepared by one of skill in the art. Preferably, the solid phase material is coated with a surfactant without washing any surfactant excess away, although the other coating reagents can be rinsed away if desired. Typically, the coating can be carried out using a variety of methods such as dipping, rolling, spraying, etc. The coating reagent-loaded solid phase material is then typically dried, for example, in air, prior to use.

Particularly desirable are solid phase materials that are coated with a surfactant, preferably a nonionic surfactant. This can be accomplished according to the procedure set forth in the Examples Section. Although not intending to be limited by theory, the addition of the surfactant is believed to increase the wettability of the solid phase material, which allows the inhibitors to soak into the solid phase material and bind thereto.

The coating reagent for the solid phase materials are preferably aqueous-based solutions, although organic solvents (alcohols, etc.) can be used, if desired. The coating reagent loading should be sufficiently high such that the sample is able to wet out the solid phase material. It should not be so high, however, that there is significant elution of the coating reagent itself. Preferably, if the coating reagent is eluted with the nucleic acid, there is no more than about 2 wt-% coating reagent in the eluted sample. Typically, the coating solution concentrations can be as low as 0.1 wt-% coating reagent in the solution and as high as 10 wt-% coating reagent in the solution.

Surfactants

Nonionic Surfactants. A wide variety of suitable nonionic surfactants are known that can be used as a lysing reagent (discussed above), an eluting reagent (discussed below), and/or as a coating on the optional solid phase material. They include, for example, polyoxyethylene surfactants, carboxylic ester surfactants, carboxylic amide surfactants, etc. Commercially available nonionic surfactants include, n-dodecanoylsucrose, n-dodecyl-β-D-glucopyranoside, n-octyl-β-D-maltopyranoside, n-octyl-β-D-thioglucopyranoside, n-decanoylsucrose, n-decyl-β-D-maltopyranoside, n-decyl-β-D-thiomaltoside, n-heptyl-β-D-glucopyranoside, n-heptyl-β-D-thioglucopyranoside, n-hexyl-β-D-glucopyranoside, n-nonyl-β-D-glucopyranoside, n-octanoylsucrose, n-octyl-β-D-glucopyranoside, cyclohexyl-n-hexyl-β-D-maltoside, cyclohexyl-n-methyl-β-D-maltoside, digitonin, and those available under the trade designations PLURONIC, TRITON, TWEEN, as well as numerous others commercially available and listed in the Kirk Othmer Technical Encyclopedia. Examples are listed in Table 1 below. Preferred surfactants are the polyoxyethylene surfactants. More preferred surfactants include octyl phenoxy polyethoxyethanol.

TABLE 1

| SURFACTANT TRADE NAME | NONIONIC SURFACTANT | SUPPLIER |
|---|---|---|
| PLURONIC F127 | Modified oxyethylated alcohol and/or oxypropylated straight chain alcohols | Sigma St. Louis, MO |
| TWEEN 20 | Polyoxyethylene (20) sorbitan monolaurate | Sigma St. Louis, MO |
| TRITON X-100 | t-Octyl phenoxy polyethoxyethanol | Sigma St. Louis, MO |
| BRIJ 97 | Polyoxyethylene (10) oleyl ether | Sigma St. Louis, MO |
| IGEPAL CA-630 | Octyl phenoxy poly (ethyleneoxy) ethanol | Sigma St. Louis, MO |
| TOMADOL 1-7 | Ethoxylated alcohol | Tomah Products Milton, WI |
| Vitamin E TPGS | d-Alpha tocopheryl polyethylene glycol 1000 | Eastman Kingsport, TN |

Also suitable are fluorinated nonionic surfactants of the type disclosed in U.S. patent Publication Ser. Nos. 2003/0139550 (Savu et al.) and 2003/0139549 (Savu et al.). Other nonionic fluorinated surfactants include those available under the trade designation ZONYL from DuPont (Wilmington, Del.).

Zwitterionic Surfactants. A wide variety of suitable zwitterionic surfactants are known that can be used as a lysing reagent, an eluting reagent, and/or as a coating on the optional solid phase material. They include, for example, alkylamido betaines and amine oxides thereof, alkyl betaines and amine oxides thereof, sulfo betaines, hydroxy sulfo betaines, amphoglycinates, amphopropionates, balanced amphopolycarboxyglycinates, and alkyl polyaminoglycinates. Proteins have the ability of being charged or uncharged depending on the pH; thus, at the right pH, a protein, preferably with a pI of about 8 to 9, such as modified Bovine Serum Albumin or chymotrypsinogen, could function as a zwitterionic surfactant. A specific example of a zwitterionic surfactant is cholamido propyl dimethyl ammonium propanesulfonate available under the trade designation CHAPS from Sigma. More preferred surfactants include N-dodecyl-N,N dimethyl-3-ammonia-1-propane sulfonate.

Cationic Surfactants. A wide variety of suitable cationic surfactants are known that can be used as a lysing reagent, an eluting reagent, and/or as a coating on the optional solid phase material. They include, for example, quaternary ammonium salts, polyoxyethylene alkylamines, and alkylamine oxides. Typically, suitable quaternary ammonium salts include at least one higher molecular weight group and two or three lower molecular weight groups are linked to a common nitrogen atom to produce a cation, and wherein the electrically-balancing anion is selected from the group consisting of a halide (bromide, chloride, etc.), acetate, nitrite, and lower alkosulfate (methosulfate, etc.). The higher molecular weight substituent(s) on the nitrogen is/are often (a) higher alkyl group(s), containing about 10 to about 20 carbon atoms, and the lower molecular weight substituents may be lower alkyl of about 1 to about 4 carbon atoms, such as methyl or ethyl, which may be substituted, as with hydroxy, in some instances. One or more of the substituents may include an aryl moiety or may be replaced by an aryl, such as benzyl or phenyl. Among the possible lower molecular weight substituents are also lower alkyls of about 1 to about 4 carbon atoms, such as methyl and ethyl, substituted by lower polyalkoxy moieties such as polyoxyethylene moieties, bearing a hydroxyl end group, and falling within the general formula:

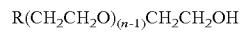

$$R(CH_2CH_2O)_{(n-1)}CH_2CH_2OH$$

where R is a (C1-C4)divalent alkyl group bonded to the nitrogen, and n represents an integer of about 1 to about 15. Alternatively, one or two of such lower polyalkoxy moieties having terminal hydroxyls may be directly bonded to the quaternary nitrogen instead of being bonded to it through the previously mentioned lower alkyl. Examples of useful quaternary ammonium halide surfactants for use in the present invention include but are not limited to methyl-bis(2-hydroxyethyl)coco-ammonium chloride or oleyl-ammonium chloride, (ETHOQUAD C/12 and O/12, respectively) and methyl polyoxyethylene (15) octadecyl ammonium chloride (ETHOQUAD 18/25) from Akzo Chemical Inc.

Anionic Surfactants. A wide variety of suitable anionic surfactants are known that can be used as a lysing reagent, an eluting reagent, and/or as a coating on the optional solid phase material. Surfactants of the anionic type that are useful include alkyl sulfonates and sulfates, such as alkyl sulfates, alkylether sulfates, alkyl sulfonates, alkylether sulfonates, alkylbenzene sufonates, alkylbenzene ether sulfates, alkylsulfoacetates, secondary alkane sulfonates, secondary alkylsulfates and the like. Many of these can include polyalkoxylate groups (e.g., ethylene oxide groups and/or propylene oxide groups, which can be in a random, sequential, or block arrangement) and/or cationic counterions such as Na, K, Li, ammonium, a protonated tertiary amine such as triethanolamine or a quaternary ammonium group. Examples include: alkyl ether sulfonates such as lauryl ether sulfates available under the trade designation POLYSTEP B12 and B22 from Stepan Company, Northfield, Ill., and sodium methyl taurate available under the trade designation NIKKOL CMT30 from Nikko Chemicals Co., Tokyo, Japan); secondary alkane sulfonates available under the trade designation HOSTAPUR SAS, which is a sodium (C14-C17)secondary alkane sulfonates (alpha-olefin sulfonates), from Clariant Corp., Charlotte, N.C.; methyl-2-sulfoalkyl esters such as sodium methyl-2-sulfo(C12-C16)ester and disodium 2-sulfo(C12-C16)fatty acid available from Stepan Company under the trade designation ALPHASTE PC-48; alkylsulfoacetates and alkylsulfosuccinates available as sodium laurylsulfoacetate (trade designation LANTHANOL LAL) and disodiumlaurethsulfosuccinate (trade designation STEPANMILD SL3), both from Stepan Co.; and alkylsulfates such as ammoniumlauryl sulfate commercially available under the trade designation STEPANOL AM from Stepan Co.

Another class of useful anionic surfactants include phosphates such as alkyl phosphates, alkylether phosphates, aralkylphosphates, and aralkylether phosphates. Many of these can include polyalkoxylate groups (e.g., ethylene oxide groups and/or propylene oxide groups, which can be in a random, sequential, or block arrangement). Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., and PPG-5 ceteth 10 phosphate available under the trade designation CRODAPHOS SG from Croda Inc., Parsipanny, N.J., as well as alkyl and alkylamidoalkyldialkylamine oxides. Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Co.

Elution Techniques

For embodiments that use a solid phase material for retaining inhibitors, the more concentrated region of the sample that includes nucleic acid-containing material (e.g., nuclei) and/or released nucleic acid can be eluted using a variety of eluting reagents. Such eluting reagents can include water (preferably RNAse free water), a buffer, a surfactant, which can be cationic, anionic, nonionic, or zwitterionic, or a strong base.

Preferably the eluting reagent is basic (i.e., greater than 7). For certain embodiments, the pH of the eluting reagent is at least 8. For certain embodiments, the pH of the eluting reagent is up to 10. For certain embodiments, the pH of the eluting reagent is up to 13. If the eluted nucleic acid is used directly in an amplification process such as PCR, the eluting reagent should be formulated so that the concentration of the ingredients will not inhibit the enzymes (e.g., Taq Polymerase) or otherwise prevent the amplification reaction.

Examples of suitable surfactants include those listed above, particularly, those known as SDS, TRITON X-100, TWEEN, fluorinated surfactants, and PLURONICS. The surfactants are typically provided in aqueous-based solutions, although organic solvents (alcohols, etc.) can be used, if desired. The concentration of a surfactant in an eluting reagent is preferably at least 0.1 weight/volume percent (w/v-%), based on the total weight of the eluting reagent. The concentration of a surfactant in an eluting reagent is preferably no greater than 1 w/v-%, based on the total weight of the eluting reagent. A stabilizer, such as polyethylene glycol, can optionally be used with a surfactant.

Examples of suitable elution buffers include TRIS-HCl, N-[2-hydroxyethyl]piperazine-N'-[2-ethanesulfonic acid] (HEPES), 3-[N-morpholino]propanesulfonic acid (MOPS), piperazine-N,N'-bis[2-ethanesulfonic acid] (PIPES), 2-[N-morpholino]ethansulfonic acid (MES), TRIS-EDTA (TE) buffer, sodium citrate, ammonium acetate, carbonate salts, and bicarbonates etc.

The concentration of an elution buffer in an eluting reagent is preferably at least 10 millimolar (mM). The concentration of a surfactant in an eluting reagent is preferably no greater than 2 weight percent (wt-%).

Typically, elution of the nucleic acid-containing material and/or released nucleic acid is preferably accomplished using an alkaline solution. Although not intending to be bound by theory, it is believed that an alkaline solution allows for improved binding of inhibitors, as compared to elution with water. The alkaline solution also facilitates lysis of nucleic acid-containing material. Preferably, the alkaline solution has a pH of 8 to 13, and more preferably 13. Examples of sources of high pH include aqueous solutions of NaOH, KOH, LiOH, quaternary nitrogen base hydroxide, tertiary, secondary or primary amines, etc. If an alkaline solution is used for elution, it is typically neutralized in a subsequent step, for example, with TRIS buffer, to form a PCR-ready sample.

The use of an alkaline solution can selectively destroy RNA, to allow for the analysis of DNA. Otherwise, RNAse can be added to the formulation to inactivate RNA, followed by heat inactivation of the RNAse. Similarly, DNAse can be added to selectively destroy DNA and allow for the analysis of RNA; however, other lysis buffers (e.g., TE) that do not destroy RNA would be used in such methods. The addition of RNAse inhibitor such as RNAsin can also be used in a formulation for an RNA preparation that is subjected to real-time PCR.

Elution is typically carried out at room temperature, although higher temperatures may produce higher yields. For example, the temperature of the eluting reagent can be up to 95° C. if desired. Elution is typically carried out within 10 minutes, although 1-3 minute elution times are preferred.

Devices and Kits

A variety of illustrative embodiments of microfluidic devices are described in U.S. Patent Publication Ser. Nos. 2002/0047003 (published Apr. 25, 2003, Bedingham et al.). These typically employ a body structure that has an integrated microfluidic channel network disposed therein. In preferred aspects, the body structure of the microfluidic devices include an aggregation of two or more separate layers which, when appropriately mated or joined together, form the microfluidic device of the invention, e.g., containing the channels and/or chambers described herein. Typically, useful microfluidic devices include a top portion, a bottom portion, and an interior portion, wherein the interior portion substantially defines the channels and chambers of the device. Typically, the chambers include valves (e.g., valve septums) and are referred to as valved chambers.

A particularly preferred device for certain embodiments herein is referred to as a variable valve device and is disclosed in Applicants' Assignee's copending U.S. patent application Ser. No. 10/734,717, filed on Dec. 12, 2003, entitled Variable Valve Apparatus and Method. In this variable valve device, the valve structures allow for removal of selected portions of the sample material located within the process chamber (i.e., the variable valved process chamber) Removal of the selected portions is achieved by forming an opening in a valve septum at a desired location.

The valve septums are preferably large enough to allow for adjustment of the location of the opening based on the characteristics of the sample material in the process chamber. If the sample processing device is rotated after the opening is formed, the selected portion of the material located closer to the axis of rotation exits the process chamber through the opening. The remainder of the sample material cannot exit through the opening because it is located farther from the axis of rotation than the opening.

The openings in the valve septum may be formed at locations based on one or more characteristics of the sample material detected within the process chamber. It may be preferred that the process chambers include detection windows that transmit light into and/or out of the process chamber. Detected characteristics of the sample material may include, e.g., the free surface of the sample material (indicative of the volume of sample material in the process chamber). Forming an opening in the valve septum at a selected distance radially outward of the free surface can provide the ability to remove a selected volume of the sample material from the process chamber.

In some embodiments, it may be possible to remove selected aliquots of the sample material by forming openings at selected locations in one or more valve septums. The selected aliquot volume can be determined based on the radial distance between the openings (measured relative to the axis of rotation) and the cross-sectional area of the process chamber between the opening.

The openings in the valve septums are preferably formed in the absence of physical contact, e.g., through laser ablation, focused optical heating, etc. As a result, the openings can preferably be formed without piercing the outermost layers of the sample processing device, thus limiting the possibility of leakage of the sample material from the sample processing device.

In one aspect, the present invention uses a valved process chamber in a sample processing device (e.g., a microfluidic device), the valved process chamber including a process chamber having a process chamber volume located between opposing first and second major sides of the sample processing device, wherein the process chamber occupies a process chamber area in the sample processing device, and wherein the process chamber area has a length and a width transverse to the length, and further wherein the length is greater than the width. The variable valved process chamber also includes a valve chamber located within the process chamber area, the valve chamber located between the process chamber volume and the second major side of the sample processing device, wherein the valve chamber is isolated from the process chamber by a valve septum separating the valve chamber and the process chamber, and wherein a portion of the process chamber volume lies between the valve septum and a first major side of the sample processing device. A detection window is located within the process chamber area, wherein the detection window is transmissive to selected electromagnetic energy directed into and/or out of the process chamber volume.

In another aspect, the present invention provides a method that allows for the selective removal of a portion of a sample from a variable valved process chamber. The method includes providing a sample processing device (e.g., a microfluidic device) as described above, providing sample material in the process chamber; detecting a characteristic of the sample material in the process chamber through the detection window; and forming an opening in the valve septum at a selected location along the length of the process chamber, wherein the selected location is correlated to the detected characteristic of the sample material. The method also includes moving only a portion of the sample material from the process chamber into the valve chamber through the opening formed in the valve septum.

The present invention also provides a kit, which can include a microfluidic device, a lysing reagent (particularly a surfactant such as a nonionic surfactant, either neat or in a solution), and instructions for separating the inhibitors from the nucleic acid.

Other components that could be included within kits of the present invention include conventional reagents such as wash solutions, coupling buffers, quenching buffers, blocking buffers, elution buffers, and the like. Other components that could be included within kits of the present invention include conventional equipment such as spin columns, cartridges, 96-well filter plates, syringe filters, collection units, syringes, and the like.

The kits typically include packaging material, which refers to one or more physical structures used to house the contents of the kit. The packaging material can be constructed by well-known methods, preferably to provide a sterile, contaminant-free environment. The packaging material may have a label that indicates the contents of the kit. In addition, the kit contains instructions indicating how the materials within the kit are employed. As used herein, the term "package" refers to a solid matrix or material such as glass, plastic, paper, foil, and the like.

"Instructions" typically include a tangible expression describing the various methods of the present invention, including lysing conditions (e.g., lysing reagent type and concentration), the relative amounts of reagent and sample to be admixed, maintenance time periods for reagent/sample admixtures, temperature, buffer conditions, and the like.

Illustrative Method 1

In another embodiment, the present invention provides a method of isolating nucleic acid from a sample, the method includes: providing a microfluidic device including a loading chamber, a valved process chamber, and a mixing chamber; providing a sample including nucleic acid-containing material and cells containing inhibitors (such nucleic acid-containing material and cells containing inhibitors may be the same or different); placing the sample in the loading chamber; contacting the sample with a first lysing reagent under conditions effective to break cell membranes and release inhibitors and form a lysed sample including nucleic acid-containing material and inhibitors; transferring the lysed sample to the valved process chamber; forming a concentrated region of the lysed sample in the valved process chamber, wherein the concentrated region of the lysed sample includes a majority of the nucleic acid-containing material and the less concentrated region includes at least a portion of the inhibitors; activating a first valve in the valved process chamber to remove at least a portion of the less concentrated region of the sample and substantially separate the concentrated region from the less concentrated region of the lysed sample thereby removing at least a portion of the inhibitors from the lysed sample; activating a second valve in the valved process chamber to transfer the separated concentrated region of the lysed sample to the mixing chamber; optionally diluting the separated concentrated region of the lysed sample with water or buffer, optionally further concentrating the diluted region to increase the concentration of nucleic acid material, optionally separating the further concentrated region, and optionally repeating this process of dilution followed by concentration and separation to reduce the inhibitor concentration to that which would not interfere with an amplification method; further lysing the nucleic acid-containing material to release nucleic acid; and optionally adjusting the pH of the sample including released nucleic acid.

The nucleic acid-containing material and cells containing inhibitors may be the same or different, although they are typically different. That is, the nucleic acid containing material and the inhibitor-containing cells could potentially be the same. For example, if the sample is a buffy coat, the nucleic acid containing material can be a white blood cell, which includes both nuclei and inhibitors. If a lysing reagent (e.g., a nonionic surfactant) is used that will lyse the cell membranes of the white blood cells but not the nuclei included therein, then the inhibitors are released as are in-tact nuclei, which is also considered to be nucleic acid-containing material as defined herein.

The nonionic surfactant, such as TRITON X-100, can be pre-deposited uniformly in the mixing chamber such that lysing occurs when the sample (e.g., blood) is mixed with the surfactant for a few minutes. In other cases, a dilute solution of surfactant can be pre-mixed with the sample (e.g., blood) prior to introduction into the mixing chamber. After mixing, the solution is centrifuged to isolate nuclei, for example. Spinning speeds, such as 400 rcf for 2 minutes, are typically desirable when using a microfluidic device, although higher spinning speeds and/or longer spinning times may be used.

In other cases, when a nonionic surfactant is not used, water or ammonium chloride can be used for lysis of red blood cells. After lysis occurs in the mixing chamber, the white blood cells can be centrifuged down at relatively low speeds.

In certain embodiments of such methods, activating a first valve in the valved process chamber to remove at least a portion of the less concentrated region of the sample includes activating a valve to remove the upper 95 volume-% of the sample.

In certain embodiments of such methods, diluting the separated concentrated region of the lysed sample with water or buffer to reduce the concentration of inhibitors, such as heme, to less than 2 micromolar can be carried out. This can be accomplished by sequential steps of 10× dilution and concentration with water or buffer. This process of diluting and concentrating (e.g., by centrifuging) can be repeated a few times until the desired level of purity of the nucleic acid-containing material is obtained. This process of diluting the inhibitor concentration while retaining the nucleic acid-containing material can be accomplished by the use of a variable valve or multiple diluent wells that are individually activated.

In certain embodiments of such methods, after the process of dilution/concentration, the clean nuclei or WBC can be lysed using a strong base such as sodium hydroxide followed by heating to denature proteins followed by neutralization of base with TRIS-HCl. Both the base and neutralization can be pre-deposited (and typically, dried-down) in a microfluidic device if desired.

In other cases, further lysing the nucleic acid-containing material to release nucleic acid includes subjecting the nucleic acid-containing material to a heating/cooling process, which can involve freezing and thawing. One or more cycles of such a lysing process can be used as desired. Typical heating temperatures and times include at least 55° C. (more typically, 95° C.) for typically 1 minute to 5 minutes and typical cooling temperatures include room temperature or below. Proteinase K and heat followed by heat inactivation of proteinase K can also be used for lysis. In these cases, Proteinase K can be pre-deposited.

In some embodiments, after lysis, the samples can be split into several wells for carrying out multiple amplification reactions, for example, looking at various SNP's for a certain disease.

As discussed above, in some cases, in order to save space on a microfluidic device, PCR enhancers, buffers, and/or alternate enzymes such as rTth polymerases can be added such that amplification proceeds even with inhibitors present in the sample undergoing PCR.

In certain embodiments of such methods, the water is RNAse-free sterile water.

The device shown in FIG. 1 can be used to carry out certain embodiments of Method 1. Referring to FIG. 1, a preferred embodiment of the microfluidic device suitable for use with these embodiment includes a loading chamber 90, an optional mixing chamber 91, valved process chambers 93, 94, and 95, a dilution reagent chamber 92, a waste chamber 97 and an optional amplification reaction chamber 96. Typically, the mixing chamber could have pre-deposited surfactant, diluting reagent chamber 92 would include water or buffer for dilution and the amplification reaction chamber could be used for lysis and amplification.

Illustrative Method 2

In another embodiment, the present invention provides a method of isolating nucleic acid from a sample, the method includes: providing a microfluidic device including a loading chamber, a valved process chamber, and a mixing chamber; providing a sample including nucleic acid-containing material, cells containing inhibitors, and optionally extracellular inhibitors (such nucleic acid-containing material and cells containing inhibitors may be the same or different); placing the sample in the loading chamber; contacting the sample with a first lysing reagent under conditions effective to break cell membranes and release inhibitors and form a lysed sample including nucleic acid-containing material and inhibitors; transferring the lysed sample to the valved process chamber; forming a concentrated region of the lysed sample in the valved process chamber, wherein the concentrated region of the lysed sample includes a majority of the nucleic acid-containing material and the less concentrated region includes at least a portion of the inhibitors; activating a first valve in the valved process chamber to remove at least a portion of the less concentrated region of the sample and substantially separate the concentrated region from the less concentrated region of the lysed sample thereby removing at least a portion of the inhibitors from the lysed sample; activating a second valve in the valved process chamber to transfer the separated concentrated region of the lysed sample to the mixing chamber; diluting the separated concentrated region of the lysed sample with water or buffer, further concentrating the diluted region to increase the concentration of nucleic acid material, separating the further concentrated region, and optionally repeating this process of dilution followed by concentration and separation to reduce the inhibitor concentration to that which would not interfere with an amplification method; further lysing the nucleic acid-containing material with a strong base and heat to release nucleic acid; and optionally adjusting the pH of the sample including released nucleic acid.

As discussed above with respect to Illustrative Method 1, the nucleic acid-containing material and cells containing inhibitors of the embodiments of Illustrative Method 2 may be the same or different, although they are typically different. That is, the nucleic acid containing material and the inhibitor-containing cells could potentially be the same.

In certain embodiments of such methods, activating a first valve in the valved process chamber to remove at least a portion of the less concentrated region of the sample includes activating a valve to remove the upper 95 volume-% of the sample.

The device shown in FIG. 1 can be used to carry out certain embodiments of Method 2. Typically, the amplification reaction chamber 96 could include a lysing reagent (e.g., a strong base), for example, in a pre-deposited (and typically, dried-down) form.

Also, as discussed above, in some cases, in order to save space on a microfluidic device, PCR enhancers, buffers, and/or alternate enzymes such as rTth polymerases can be added such that amplification proceeds even with inhibitors present in the sample undergoing PCR.

Additional Embodiments

In addition to reducing the amount of inhibitors using concentration/separation/optional dilution steps, for example, as described herein, inhibitors can optionally be removed using solid phase materials as disclosed in U.S. patent application Ser. No. 10/852,645, filed on May 24, 2004, entitled METHODS FOR NUCLEIC ACID ISOLATION AND KITS USING SOLID PHASE MATERIAL.

In certain embodiments, placing the sample in the loading chamber of a microfluidic device occurs prior to contacting the sample with a first lysing reagent. Alternatively, placing the sample in the loading chamber occurs after contacting the sample with a first lysing reagent. The first lysing reagent can be water or a nonionic surfactant, for example.

If additional lysing is needed to release nucleic acid from nucleic acid-containing material (e.g., nuclei), other lysing conditions can be used. For example, this includes subjecting the nucleic acid-containing material to a strong base with optional heating. The strong base is typically NaOH, but can be others such as KOH, LiOH, NH$_4$OH, as well as primary, secondary, or tertiary amines. Typically, the temperature is at room temperature. If a base is used, the sample containing the released nucleic acid may need to have its pH adjusted, particularly if the nucleic acid is to be subjected to a subsequent amplification process. Thus, certain embodiments of the invention include adjusting the pH of the sample typically to at least 7.5, and typically to no greater than 9.

In certain embodiments, the first lysing reagent is a nonionic surfactant. In certain embodiments of such methods, the loading chamber includes the first lysing reagent (e.g., pre-deposited (and typically, dried-down) nonionic surfactant) and contacting the sample with a first lysing reagent occurs upon placing the sample in the loading chamber.

Alternatively, the sample could be transferred to a subsequent processing chamber with the first lysing reagent (preferably, a nonionic surfactant) therein. For example, contacting the sample with a first lysing reagent (preferably, a nonionic surfactant) occurs in a mixing chamber with sufficient mixing to break cell membranes and release nuclei and inhibitors to form a lysed sample. It should be understood that if a "first" lysing reagent is used, the methods do not necessarily require the use of a "second" lysing reagent; rather, the term "first lysing reagent" is used herein to distinguish from any additional lysing reagents if used.

As stated above, the addition of sucrose in a buffer (particularly, a TRIS buffer) may help in the isolation of nuclei. The buffer could also include magnesium salts and surfactants such as TRITON X-100. This may also provide a good medium for lysis of white blood cells. Furthermore, in certain cases, when the nuclei need to be archived, particularly within a microfluidic device, using a nuclei storage buffer may be useful. The nuclei storage buffer could include sucrose, magnesium salts, EDTA, dithiothrietol, 4-(2-aminoethyl)benzenesulfonyl fluoride (AEBSF), and/or glycerol, for example, in a buffer (e.g., TRIS buffer) and would allow for stable storage of nuclei.

In certain embodiments, forming a concentrated region of the sample in the valved process chamber includes centrifuging the sample in the process chamber. Typically, separating the concentrated region from the less concentrated of the sample includes transferring the less concentrated region of the sample through the valve to a waste bin.

In addition to solid phase materials mentioned above, other types of solid phase materials, particularly beads, can be introduced into a microfluidic device in a variety of embodiments of the present invention. For example, beads can be functionalized with the appropriate groups to isolate specific cells, viruses, bacteria, proteins, nucleic acids, etc. The beads can be segregated from the sample by centrifugation and subsequent separation. The beads could be designed to have the appropriate density and sizes (nanometers to microns) for segregation. For example, in the case of viral capture, beads that recognize the protein coat of a virus can be used to capture and concentrate the virus prior to or after removal of small amounts of residual inhibitors from a serum sample.

The inhibitors can be removed after viral capture by a series of dilution and centrifugation steps (and optionally using solid phase materials as disclosed in U.S. patent application Ser. No. 10/852,645, filed on May 24, 2004, entitled METHODS FOR NUCLEIC ACID ISOLATION AND KITS USING SOLID PHASE MATERIAL. Such solid phase materials can be used with various methods and samples described herein.

Nucleic acids can be extracted out of the segregated viral particles by lysis. Thus, the beads could provide a way of concentrating relevant material in a specific region within a microfluidic device, also allowing for washing of irrelevant materials and elution of relevant material from the captured particle.

Examples of such beads include, but are not limited to, crosslinked polystyrene beads available under the trade designation CHELEX from Bio-Rad Laboratories, Inc. (Hercules, Calif.), crosslinked agarose beads with tris(2-aminoethyl)amine, iminodiacetic acid, nitrilotriacetic acid, polyamines and polyimines as well as the chelating ion exchange resins commercially available under the trade designation DUOLITE C-467 and DUOLITE GT73 from Rohm and Haas (Philadelphia, Pa.), AMBERLITE IRC-748, DIAION CR11, DUOLITE C647. These beads are also suitable for use as the solid phase material as discussed above.

Other examples of beads include those available under the trade designations GENE FIZZ (Eurobio, France), GENE RELEASER (Bioventures Inc., Murfreesboro, Tenn.), and BUGS N BEADS (GenPoint, Oslo, Norway), as well as Zymo's beads (Zymo Research, Orange, Calif.) and DYNAL beads (Dynal, Oslo, Norway).

Other materials are also available for pathogen capture. For example, polymer coatings can also be used to isolate specific cells, viruses, bacteria, proteins, nucleic acids, etc. in certain embodiments of the invention. These polymer coatings could directly be spray-jetted, for example, onto the cover film of a microfluidic device.

Viral particles can be captured onto beads by covalently attaching antibodies onto bead surfaces. The antibodies can be raised against the viral coat proteins. For example, DYNAL beads can be used to covalently link antibodies. Alternatively, synthetic polymers, for example, anion-exchange polymers, can be used to concentrate viral particles. Commercially available resins such as viraffinity (Biotech Support Group, East Brunswick, N.J.) can be used to coat beads or applied as polymer coatings onto select locations in microfluidic device to concentrate viral particles. BUGS N BEADS (GenPoint, Oslo, Norway) can, for example, be used for extraction of bacteria. Here, these beads can be used to capture bacteria such as *Staphylococcus, Streptococcus, E. coli, Salmonella*, and *Clamydia* elementary bodies.

Thus, in one embodiment of the present invention when the sample includes viral particles or other pathogens (e.g., bacteria), a microfluidic device can include solid phase material in the form of viral capture beads or other pathogen capture material. In this method, the sample contacts the viral capture beads prior to the concentration step. More specifically, in one case, the viral capture beads can be used only for concentration of virus or bacteria, for example, followed by segregation of beads to another chamber, ending with lysis of virus or bacteria. In another case, the beads can be used for concentration of virus or bacteria, followed by lysis and capture of nucleic acids onto the same bead, dilution of beads, concentration of beads, segregation of beads, and repeating the process multiple times prior to elution of captured nucleic acid.

Alternatively, if beads (or other viral capture material) are not the method of choice for viral capture (or other pathogen capture), then one may choose to pellet out (i.e., concentrate) viral particles from serum or plasma using an ultracentrifuge. These concentrated viral particles can be transferred to the microfluidic device for lysing (e.g., with a surfactant with the addition of an RNAse inhibitor, for example), if viral RNA needs to be isolated followed by an amplification reaction (RT-PCR).

Beads can be used directly in a PCR reaction chamber if desired. Alternatively, if beads are used, an eluting reagent may be used. Such eluting reagents can include water (preferably RNAse-free sterile water), a buffer, a surfactant, which can be cationic, anionic, nonionic, or zwitterionic, or a strong base.

Preferably the eluting reagent is basic (i.e., greater than 7). For certain embodiments, the pH of the eluting reagent is at least 8. For certain embodiments, the pH of the eluting reagent is up to 10. For certain embodiments, the pH of the eluting reagent is up to 13. If the eluted nucleic acid is used directly in an amplification process such as PCR, the eluting reagent should be formulated so that the concentration of the ingredients will not inhibit the enzymes (e.g., Taq Polymerase) or otherwise prevent the amplification reaction.

Examples of suitable surfactants include those listed above, particularly, those known as SDS, TRITON X-100, TWEEN, fluorinated surfactants, and PLURONICS. The surfactants are typically provided in aqueous-based solutions, although organic solvents (alcohols, etc.) can be used, if desired. The concentration of a surfactant in an eluting reagent is preferably at least 0.1 weight/volume percent (w/v-%), based on the total weight of the eluting reagent. The concentration of a surfactant in an eluting reagent is preferably no greater than 1 w/v-%, based on the total weight of the eluting reagent. A stabilizer, such as polyethylene glycol, can optionally be used with a surfactant.

Examples of suitable elution buffers include TRIS-HCl, N-[2-hydroxyethyl]piperazine-N'-[2-ethanesulfonic acid] (HEPES), 3-[N-morpholino]propanesulfonic acid (MOPS), piperazine-N,N'-bis[2-ethanesulfonic acid] (PIPES), 2-[N-morpholino]ethansulfonic acid (MES), TRIS-EDTA (TE) buffer, sodium citrate, ammonium acetate, carbonate salts, and bicarbonates etc.

The concentration of an elution buffer in an eluting reagent is preferably at least 10 millimolar (mM). The concentration of a surfactant in an eluting reagent is preferably no greater than 2 weight percent (wt-%).

Typically, elution of the nucleic acid-containing material and/or released nucleic acid is preferably accomplished using an alkaline solution. Although not intending to be bound by theory, it is believed that an alkaline solution allows for improved binding of inhibitors, as compared to elution with water. The alkaline solution also facilitates lysis of nucleic acid-containing material. Preferably, the alkaline solution has a pH of 8 to 13, and more preferably 13. Examples of sources of high pH include aqueous solutions of NaOH, KOH, LiOH, quaternary nitrogen base hydroxide, tertiary, secondary or primary amines, etc. If an alkaline solution is used for elution, it is typically neutralized in a subsequent step, for example, with TRIS buffer, to form a PCR-ready sample.

The use of an alkaline solution can selectively destroy RNA, to allow for the analysis of DNA. Otherwise, RNAse can be added to the formulation to inactivate RNA, followed by heat inactivation of the RNAse. Similarly, DNAse can be added to selectively destroy DNA and allow for the analysis of RNA; however, other lysis buffers (e.g., TE) that do not destroy RNA would be used in such methods. The addition of RNAse inhibitor such as RNAsin can also be used in a formulation for an RNA preparation that is subjected to real-time PCR.

Elution is typically carried out at room temperature, although higher temperatures may produce higher yields. For example, the temperature of the eluting reagent can be up to 95° C. if desired. Elution is typically carried out within 10 minutes, although 1-3 minute elution times are preferred.

If the downstream application of the nucleic acid is subjecting it to an amplification process such as PCR, then all reagents used in the method are preferably compatible with such process (e.g., PCR compatible). Furthermore, the addition of PCR facilitators may be useful, especially for diagnostic purposes. Also, heating of the material to be amplified prior to amplification can be beneficial.

In embodiments in which the inhibitors are not completely removed, the use of buffers, enzymes, and PCR facilitators can be added that help in the amplification process in the presence of inhibitors. For example, enzymes other than Taq Polymerase, such as rTth, that are more resistant to inhibitors can be used, thereby providing a huge benefit for PCR amplification. The addition of Bovine Serum Albumin, betaine, proteinase inhibitors, bovine transferrin, etc. can be used as they are known to help even further in the amplification process. Alternatively, one can use a commercially available product such as Novagen's Blood Direct PCR Buffer kit (EMD Biosciences, Darmstadt, Germany) for direct amplification from whole blood without the need for extensive purification.

Objects and advantages of this invention are further illustrated by the following examples, but the particular materials and amounts thereof recited in these examples, as well as other conditions and details, should not be construed to unduly limit this invention.

EXAMPLES

Example 1

Procedure for Isolation of Genomic DNA from Whole Blood Without the Use of a Chelating Solid Phase Material One (1) µL of neat TRITON X-100 was added to one hundred (100) µL of whole blood. The solution was incubated at room temperature (approximately 21° C.) for about 5 minutes, vortexing the solution intermittently (for approximately 5 seconds every 20 seconds). The solution was investigated to make sure that it was transparent before proceeding to the next step. The solution was spun in an Eppendorf Model 5415D centrifuge at 400 rcf for about 10 minutes. The supernatant was separated and discarded, leaving about two (2) µL of concentrated material at the bottom of the centrifuge tube. This concentrated material was transferred to a new microcentrifuge tube. Ten (10) µL of 0.1 M NaOH was added, mixed, and incubated at room temperature (approximately 21° C.) for approximately 5 minutes. A 2 µL aliquot was removed and added to 10 µL of 40 mM TRIS-HCl (pH 7.4).

Example 2A

Effect of Inhibitor/DNA on PCR: Varying Inhibitor Concentration with Fixed DNA Concentration A dilution series of inhibitors were made prior to spiking with clean human genomic DNA in order to study the effect of inhibitor on PCR. To 10 µL of 15 nanograms per microliter (ng/µL) human genomic DNA, 1 µL of different Mix I (neat or dilutions thereof) was added (Samples 2—no inhibitor added, 2D—neat, 2E—1:10, 2F—1:30, 2G—1:100, 2H—1:300) and vortexed. Two (2) µL aliquots of each sample were taken for 20 µL PCR. The results are shown in Table 2.

Mix I: one hundred (100) µL of whole blood was added to 1 µL of neat TRITON X-100. The solution was incubated at room temperature (approximately 21° C.) for about 5 minutes, vortexing the solution intermittently (for approximately 5 seconds every 20 seconds). The solution was investigated to make sure that it was transparent before proceeding to the next step. The solution was spun in an Eppendorf Model 5415D centrifuge at 400 rcf for about 10 minutes. Approximately 80 µL from the top of the microcentrifuge tube and designated Mix I.

Example 2B

Effect of Inhibitor/DNA on PCR: Varying DNA Concentration with Fixed Inhibitor Concentration To 10 µL of human genomic DNA, 1 µL of 1:3 diluted Mix I (described above) was added. DNA concentrations that were examined were the following: Samples 2J—15 ng/µL, 2K—7.5 ng/µL, 2L—3.75 ng/µL, 2M—1.5 ng/µL. Two (2) µL aliquots of each sample were taken for 20 µL PCR. The results are shown in Table 2.

Example 2C

Effect of Inhibitor/DNA on PCR: DNA with No Added Inhibitor

The following samples were prepared with 1 µL of water added to each DNA sample instead of inhibitor: Samples 2N—15 ng/µL, 2P—7.5 ng/µL, 2Q—3.75 ng/µL, 2R—1.5 ng/µL. Two (2) µL aliquots of each sample were taken for 20 µL PCR. The results are shown in Table 2.

TABLE 2

| Sample No. | Ct (duplicate samples) |
|---|---|
| 2 | 19.10 |
|   | 19.06 |
| 2D | 13.94 |
|   | 29.50 |
| 2E | 27.39 |
|   | 26.22 |
| 2F | 21.44 |
|   | 20.66 |
| 2G | 19.90 |
|   | 19.30 |
| 2H | 19.90 |
|   | 20.08 |
| 2J | 28.45 |
|   | 28.61 |
| 2K | 29.16 |
|   | 30.22 |
| 2L | 30.47 |
|   | 29.96 |
| 2M | 28.43 |
|   | 26.16 |
| 2N | 20.05 |
|   | 19.80 |
| 2P | 20.74 |
|   | 20.54 |
| 2Q | 21.95 |
|   | 21.88 |
| 2R | 22.67 |
|   | 23.10 |

Example 3

Procedure for Isolation of Genomic DNA from Whole Blood: Using Heat

One (1) µL of neat TRITON X-100 was added to one hundred (100) µL of whole blood. The solution was incubated at room temperature (approximately 21° C.) for about 5 minutes, vortexing the solution intermittently (approximately 5 seconds every 20 seconds). The solution was investigated to make sure that it was transparent before proceeding to the next step. The solution was spun in an Eppendorf Model 5415D centrifuge at 400 rcf for about 10 minutes. The supernatant was separated and discarded, leaving about two (2) µL of concentrated material at the bottom of the centrifuge tube. This concentrated material was transferred to a new microcentrifuge tube. Ten (10) µL of 0.1 M NaOH was added to the solution and incubated at room temperature (approximately 21° C.) for about 5 minutes. The solution for heated at 95° C. for 3 minutes. A 2 µL aliquot was removed and added to 10 µL of 40 mM TRIS-HCl (pH 7.4).

Example 4

Procedure for Isolation of Genomic DNA from Whole Blood Using RNase-Free Water Dilution Two (2) µL of neat TRITON X-100 was added to one hundred (100) µL of whole blood. The solution was incubated at room temperature (approximately 21° C.) for about 5 minutes, vortexing the solution intermittently (for approximately 5 seconds every 20 seconds). The solution was investigated to make sure that it was transparent before proceeding to the next step. The solution was spun in an Eppendorf Model 5415D centrifuge at 400 rcf for about 2 minutes. The supernatant was separated and discarded, leaving about five (5) µL of concentrated material at the bottom of the centrifuge tube. To the last 5 µL of concentrated material, 95 µL of RNase-free sterile water was added. The sample was mixed until the color became uniform. The solution was spun in an Eppendorf Model 5415D centrifuge at 400 rcf for about 2 minutes. A 95 µL of the solution on the top was separated and discarded, leaving about five (5) µL of concentrated material at the bottom of the centrifuge tube. To the last 5 µL of concentrated material, 95 µL of RNase-free sterile water was added. The sample was mixed until the color became uniform. The solution was spun in an Eppendorf Model 5415D centrifuge at 400 rcf for about 2 minutes. To the last 5 µL of concentrated material, one (1) µL of 0.5 M NaOH was added. After 1 min incubation, the sample was heated for 3 min at 95° C. A 1.5 µL aliquot of 1 M TRIS-HCl (pH 7.4) was added to 6 µL of sample.

Example 5

Procedure for Isolation of Genomic DNA from Whole Blood Using RNase-Free Water Dilution: Sample Separation in Separating Chamber of a Microfluidic Device Two (2) µL of neat TRITON X-100 was added to one hundred (100) µL of whole blood. The solution was incubated at room temperature (approximately 21° C.) for about 5 minutes, vortexing the solution intermittently (for approximately 5 seconds every 20 seconds). The solution was investigated to make sure that it was transparent before proceeding to the next step. The solution was placed in a separating chamber of a microfluidic device as described in Applicants' Assignee's copending U.S. patent application Ser. No. 10/734,682, filed Dec. 12, 2003 (FIG. 1), and was spun at 4000 rpm for 4 min. A 95 µL aliquot of the solution from the top was removed and discarded. Last five (5) µL containing concentrated material was transferred to another clean separating chamber. A 95 µL of RNase-free sterile water was added to 5 µL. The solution was mixed up and down 2-3 times in a pipette tip. The sample was spun at 4000 for 4 min. A 95 µL aliquot of the solution from the top was removed and discarded. Last five (5) µL containing concentrated material was transferred to another clean separating chamber. A 95 µL of RNase-free sterile water was added to 5 µL. The solution was mixed up and down 2-3 times in a pipette tip. The sample was spun at 4000 for 4 min. A 95 µL aliquot of the solution from the top was removed and discarded. Last five (5) µL containing concentrated material was transferred to a clean microcentrifuge tube. To 5 µL of concentrated material, one (1) µL of 0.5 M NaOH was added. After 1 min incubation, the sample was heated for 3 min at 95° C. A 1.5 µL aliquot of 1 M TRIS-HCl (pH 7.4) was added to 6 µL of sample.

Example 6

Procedure for Isolation of Genomic DNA from Whole Blood Using RNAse-Free Water Dilution: Mixing with TRITON X-100 in a Mixing Chamber of a Microfluidic Device Ten (10) µL of 10% TRITON X-100 solution was dried overnight on the cover film of the mixing chamber of a microfluidic device as described in Applicants' Assignee's copending U.S. patent application Ser. No. 10/734,682, filed Dec. 12, 2003 (FIG. 1). One hundred (100) µL of whole blood was added to the mixing chamber. The solution was mixed for about 5 minutes. The solution was investigated to make sure that it was transparent before proceeding to the next step. The solution was transferred into a clean microcentrifuge tube and spun in an Eppendorf Model 5415D centrifuge at 400 rcf for about 2 minutes. Ninety five (95) µL of solution from the top was separated and discarded, leaving about five (5) µL of concentrated material at the bottom of the centrifuge tube. To the last 5 µL of concentrated material, 95 µL of RNase-free sterile water was added. The sample was mixed until the color became uniform. The solution was spun in an Eppendorf Model 5415D centrifuge at 400 rcf for about 2 minutes. A 95 µL aliquot of the solution from the top was removed and discarded, leaving about five (5) µL of concentrated material at the bottom of the centrifuge tube. To the last 5 µL of concentrated material, 95 µL of RNase-free sterile water was added. The sample was mixed until the color became uniform. The solution was spun in an Eppendorf Model 5415D centrifuge at 400 rcf for about 2 minutes. A 95 µL aliquot of the solution from the top was removed and discarded, leaving about five (5) µL of concentrated material at the bottom of the centrifuge tube. To the last 5 µL of concentrated material, one (1) µL of 0.5 M NaOH was added. After 1 min incubation, the sample was heated for 3 min at 95° C. A 1.5 µL aliquot of 1 M TRIS-HCl (pH 7.4) was added to 6 µL of sample.

Example 7

Procedure for Isolation of Genomic DNA from Whole Blood

Five (5) µL of whole blood was added to the ten (10) µL of 10 mM NaOH. After 1 min incubation, the sample was heated for 3 min at 95° C. A 5 µL aliquot of 16 mM TRIS-HCl (pH 7.4) was added to 10 µL of sample.

Example 8

Procedure for Isolation of Genomic DNA from Whole Blood Using RNase-Free Water Dilution One hundred (100) µL of 1% IGEPAL CA-630 (Sigma, St. Louis) was added to one hundred (100) µL of whole blood. The solution was vortexed intermittently (for approximately 5 seconds every 20 seconds). The solution was investigated to make sure that it was transparent before proceeding to the next step. The solution was spun in an Eppendorf Model 5415D centrifuge at 400 rcf for about 2 minutes. A 195 µL of the solution on the top was separated and discarded, leaving about five (5) µL of concentrated material at the bottom of the centrifuge tube. To the last 5 µL of concentrated material, 45 µL of RNase-free sterile water was added. The sample was mixed until the color became uniform. The solution was spun in an Eppendorf Model 5415D centrifuge at 400 rcf for about 2 minutes. A 45 µL of the solution on the top was separated and discarded, leaving about five (5) µL of concentrated material at the bottom of the centrifuge tube. To the last 5 µL of concentrated material, 45 µL of RNase-free sterile water was added. The sample was mixed until the color became uniform. The solution was spun in an Eppendorf Model 5415D centrifuge at 400 rcf for about 2 minutes. To the last 5 µL of concentrated material, one (1) µL of 0.5 M NaOH was added. After 1 min incubation, the sample was heated for 3 min at 95° C. A 1.5 µL aliquot of 1 M TRIS-HCl (pH 7.4) was added to 6 µL of sample. A 42.5 µL aliquot of water was added to the sample.

RESULTS

Table 3 reports results that were obtained on ABI 7700 QPCR Machine (Applera, Foster City, Calif.) following the instructions in QuantiTech SYBR Green PCR Handbook on p. 10-12 for preparation of a 10 µL PCR sample (2 µL of sample in 10 µL SYBR Green Master Mix, 4 µL β-actin, 4 µL of water) for Examples 1-3; Results for Examples 4-7 were obtained on LightCycler 2.0 (Roche Applied Science, Indianapolis, Ind.) following the instructions in LightCycler Factor V Leiden Mutation Kit's package insert on p. 2-3 for preparation of a 10 µL PCR sample (2.5 µL of sample in 5.5 µL of RNAse-free sterile water, 1 µL of 10× Factor V Leiden Reaction Mix and 1 µL of 10× Factor V Leiden Mutation Detection Mix); Results for Example 8 were obtained on LightCycler 2.0 (Roche Applied Science, Indianapolis, Ind.) following the instructions in LightCycler Control DNA Kit package insert on p. 8-10 for preparation of a 10 µL PCR sample (1 µL of sample in 5.8 µL of RNase-free sterile water and 1 µL of β-Globin Primer Mix from LightCycler Control DNA Kit, and in 1.2 µL of MgCl$_2$ and 1 µL of 10× LightCycler DNA Master SYBR Green I from LightCycler DNA Master SYBR Green I Kit). One (1)% agarose gel (brightness of band—+ faint, +++ bright) was run on Horizon 11-14 Electrophoresis Machine (Gibco BRL, Gaithersburg, Md.). Spectra measurements were run on a SpectraMax Plus[384] spectrophotometer at 405 nm (Molecular Devices Corporation, Sunnyvale, Calif.). Two, three or four values for each sample represent duplicates, triplicates, or quadruplicates.

TABLE 3

| Samples | Ct | Band | 405 nm (avg) |
|---|---|---|---|
| 1.5 ng/µL human genomic DNA in 0.1 M NaOH/40 mM TRIS-HCl buffer | 16.92<br>20.67 | +++<br>+++ | — |
| 1.5 ng/µL human genomic DNA in water | 19.01<br>18.67 | +++<br>+++ | 0 |
| 1.5 ng/µL human genomic DNA in water | 16.18<br>16.28 | +++<br>+++ | — |
| Example 1 | 26.64 26.18 | ++<br>++ | 1.3 |
| Examples 2A and 2B Mix I diluted 1:36 | — | − | 2.63 |

TABLE 3-continued

| Samples | Ct | Band | 405 nm (avg) |
|---|---|---|---|
| Examples 2A and 2B Mix I diluted 1:360 | — | – | 0.38 |
| Examples 2A and 2B Mix I diluted 1:3600 | — | – | 0.036 |
| Examples 2A and 2B Mix I diluted 1:36000 | — | – | 0 |
| Example 3 | | +++ | — |
| Example 4 | 21.40, 21.31 | – | — |
| Example 5 | 25.83 | – | — |
| Example 6 | 21.89 | – | — |
| Example 7* | 30.35, 30.56 | – | — |
| Example 8* | 20.02, 19.96, 19.63, 19.82 | – | — |

*Positive Control for Examples 7 and 8 was DNA extracted from two hundred (200) μL of whole blood following "Blood and Body Fluid Spin Protocol" described in QIAamp DNA Blood Mini Kit Handbook p. 27, eluting in 200 μL of water and had Ct value of 20-21. Negative Control (NTC or no template control) did not amplify in these experiments.

The complete disclosures of the patents, patent documents, and publications cited herein are incorporated by reference in their entirety as if each were individually incorporated. Various modifications and alterations to this invention will become apparent to those skilled in the art without departing from the scope of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of separating nucleic acid from inhibitors in a sample, the method comprising:
   providing a microfluidic device comprising a valved process chamber, at least one additional chamber, and an axis of rotation;
   providing a sample comprising nucleic acid bound to beads and/or nucleic acid-containing material bound to beads, and inhibitors;
   placing the sample in the microfluidic device;
   positioning the sample in the valved process chamber;
   forming a concentrated region and a less concentrated region of the sample in the valved process chamber by rotating the microfluidic device about the axis of rotation, wherein the concentrated region of the sample comprises a majority of the beads with nucleic acid and/or nucleic acid-containing material bound thereto, and the less concentrated region comprises at least a portion of the inhibitors; and
   forming an opening in a valve septum of the valved process chamber at a desired location and rotating the microfluidic device to remove at least a portion of the less concentrated region of the sample and substantially separate the concentrated region from the less concentrated region of the sample thereby removing at least a portion of the inhibitors from the sample.

2. The method of claim 1, further comprising:
   diluting the separated concentrated region of the sample with water or buffer, further concentrating the diluted region to increase the concentration of beads with nucleic acid and/or nucleic acid-containing material bound thereto, separating the further concentrated region, and repeating this process of dilution followed by concentration and separation to reduce the inhibitor concentration to that which would not interfere with an amplification process;
   lysing nucleic acid-containing material, if present, with optional heating to release nucleic acid;
   adjusting the pH of the sample comprising nucleic acid;
   amplifying a particular nucleic acid in the sample; and
   detecting the particular nucleic acid.

3. A method of isolating nucleic acid from a sample, the method comprising:
   providing a microfluidic device comprising a valved process chamber, at least one additional chamber, and an axis of rotation;
   providing a sample comprising nucleic acid and inhibitors;
   placing the sample in the microfluidic device;
   positioning the sample in the valved process chamber;
   forming a concentrated region and a less concentrated region of the sample in the valved process chamber by rotating the microfluidic device about the axis of rotation, wherein the concentrated region of the sample comprises a majority of the nucleic acid-containing material, and the less concentrated region comprises at least a portion of the inhibitors; and
   forming an opening in a valve septum of the valved process chamber at a desired location and rotating the microfluidic device to remove at least a portion of the less concentrated region of the sample and substantially separate the concentrated region from the less concentrated region of the sample thereby removing at least a portion of the inhibitors from the sample.

4. The method of claim 3, wherein forming an opening in a valve septum includes forming a first opening in a valve septum, and further comprising forming a second opening in the valve septum of the valved process chamber at a desired location and rotating the microfluidic device to transfer the separated concentrated region of the sample to at least one additional chamber.

5. The method of claim 4, wherein forming a first opening in a valve septum of the valved process chamber at a desired location includes forming a first opening in a valve septum of the valved process chamber at a first location, and wherein forming a second opening in the valve septum in the valved process chamber includes forming a second opening in the valve septum of the valved process chamber at a second location, wherein the second location is located farther from the axis of rotation than the first location.

6. The method of claim 3, further comprising:
   diluting the separated concentrated region of the sample with water or buffer, further concentrating the diluted region to increase the concentration of nucleic acid material, separating the further concentrated region, and repeating this process of dilution followed by concentration and separation to reduce the inhibitor concentration to that which would not interfere with an amplification process;
   lysing nucleic acid-containing material, if present, with optional heating to release nucleic acid;
   adjusting the pH of the sample comprising nucleic acid;
   amplifying a particular nucleic acid in the sample; and
   detecting the particular nucleic acid.

7. The method of claim 6, wherein adjusting the pH comprises adjusting the pH to be within a range of 7.5 to 9.

8. The method of claim 3, wherein the sample comprises nucleic acid-containing material, cells containing inhibitors, and extracellular inhibitors.

9. The method of claim 3, wherein forming an opening in a valve septum of the valved process chamber comprises forming an opening in a valve septum to remove the upper 95 volume-% of the sample.

10. The method of claim 3, wherein the microfluidic device includes a solid phase material.

11. The method of claim 3, wherein the solid phase material comprises pathogen capture material and the sample comprises one or more pathogens.

12. The method of claim 11, wherein forming a concentrated region and a less concentrated region of the sample in the valved process chamber comprises contacting the sample with the pathogen capture material.

13. The method of claim 3, wherein forming a concentrated region and a less concentrated region of the sample in the valved process chamber comprises centrifuging the sample in the process chamber.

14. The method of claim 3, wherein:
the sample comprises blood serum or plasma, and one or more pathogens;
the method further comprises concentrating the one or more pathogens prior to placing the sample in the microfluidic device; and
placing the sample in the microfluidic device comprises placing the concentrated one or more pathogens into the microfluidic device.

15. A method of isolating nucleic acid from a sample, the method comprising:
providing a microfluidic device comprising a valved process chamber, at least one additional chamber, and an axis of rotation;
providing a sample comprising nucleic acid-containing material, cells containing inhibitors, and optionally extracellular inhibitors;
placing the sample in the microfluidic device;
contacting the sample with a first lysing reagent under conditions effective to break cell membranes and release inhibitors and form a lysed sample comprising nucleic acid-containing material and inhibitors;
positioning the lysed sample in the valved process chamber;
forming a concentrated region and a less concentrated region of the lysed sample in the valved process chamber by rotating the microfluidic device, wherein the concentrated region of the lysed sample comprises a majority of the nucleic acid-containing material and the less concentrated region comprises at least a portion of the inhibitors; and
forming an opening in a valve septum of the valved process chamber and rotating the microfluidic device about the axis of rotation to remove at least a portion of the less concentrated region of the sample and substantially separate the concentrated region from the less concentrated region of the lysed sample thereby removing at least a portion of the inhibitors from the lysed sample.

16. The method of claim 15, further comprising:
diluting the separated concentrated region of the lysed sample with water or buffer, further concentrating the diluted region to increase the concentration of nucleic acid material, separating the further concentrated region, and repeating this process of dilution followed by concentration and separation to reduce the inhibitor concentration to that which would not interfere with an amplification method;
further lysing the nucleic acid-containing material to release nucleic acid; and
adjusting the pH of the sample comprising released nucleic acid.

17. The method of claim 16, wherein further lysing the nucleic acid-containing material to release nucleic acid comprises subjecting the nucleic acid-containing material to a heating/cooling process.

18. The method of claim 16, wherein further lysing the nucleic acid-containing material to release nucleic acid comprises subjecting the nucleic acid-containing material to a strong base with optional heating, wherein the strong base has a pH that is effective for an alkaline lysis.

19. The method of claim 16, wherein adjusting the pH of the sample comprising the released nucleic acid includes adjusting the pH to be within a range of 7.5 to 9.

20. The method of claim 16, further comprising transferring the sample comprising released nucleic acid to an amplification reaction chamber.

21. The method of claim 20, further comprising amplifying the released nucleic acid.

22. The method of claim 15, further comprising:
diluting the separated concentrated region of the lysed sample with water or buffer, further concentrating the diluted region to increase the concentration of nucleic acid material, separating the further concentrated region, and repeating this process of dilution followed by concentration and separation to reduce the inhibitor concentration to that which would not interfere with an amplification method;
further lysing the nucleic acid-containing material with a strong base and heat to release nucleic acid, wherein the strong base has a pH that is effective for an alkaline lysis procedure; and
adjusting the pH of the sample comprising released nucleic acid.

23. The method of claim 15, further comprising diluting the separated concentrated region of the lysed sample with water to reduce the concentration of heme to less than 2 micromolar.

24. The method of claim 23, wherein the water is RNAse-free sterile water.

25. The method of claim 15, wherein forming an opening in a valve septum of the valved process chamber comprises forming an opening in a valve septum to remove the upper 95 volume-% of the sample.

26. The method of claim 15, wherein the nucleic acid-containing material comprises nuclei.

27. The method of claim 15, wherein placing the sample in the microfluidic device occurs prior to contacting the sample with a first lysing reagent.

28. The method of claim 15, wherein the microfluidic device further comprises a loading chamber, wherein the loading chamber comprises the first lysing reagent, wherein placing the sample in the microfluidic device includes placing the sample in the loading chamber, and wherein contacting the sample with a first lysing reagent occurs upon placing the biological sample in the loading chamber.

29. The method of claim 15, wherein placing the sample in the microfluidic device occurs after contacting the sample with a first lysing reagent.

30. The method of claim 15, wherein forming a concentrated region and a less concentrated region of the sample in the valved process chamber comprises centrifuging the sample in the process chamber.

31. The method of claim 15, wherein the first lysing reagent is a nonionic surfactant.

32. The method of claim 15, wherein the sample comprises nucleic acid-containing material, cells containing inhibitors, and extracellular inhibitors.

33. The method of claim 1, wherein forming an opening in a valve septum includes forming a first opening in a valve septum, and further comprising forming a second opening in the valve septum of the valved process chamber at a desired location and rotating the microfluidic device to transfer the separated concentrated region of the sample to at least one additional chamber.

34. The method of claim 1, wherein forming a first opening in a valve septum of the valved process chamber at a desired location includes forming a first opening in a valve septum of the valved process chamber at a first location, and wherein forming a second opening in the valve septum in the valved process chamber includes forming a second opening in the valve septum of the valved process chamber at a second location, wherein the second location is located farther from the axis of rotation than the first location.

* * * * *